US007785593B2

(12) United States Patent
Barske et al.

(10) Patent No.: US 7,785,593 B2
(45) Date of Patent: Aug. 31, 2010

(54) ANTIBODY (11C7) ANTI NOGO A AND ITS PHARMACEUTICAL USE

(75) Inventors: Carmen Barske, Loerrach (DE); Anis Khusro Mir, Bartenheim (FR); Thomas Oertle, Gerra/Gambarogno (CH); Lisa Schnell, Zürich (CH); Martin E. Schwab, Zürich (CH); Alessandra Vitaliti, Bedigliora (CH); Mauro Zurini, Binningen (CH)

(73) Assignees: Novartis AG, Basel (CH); University of Zurich, Zurich (CH)

( * ) Notice: Subject to any disclaimer, the term of this patent is extended or adjusted under 35 U.S.C. 154(b) by 1059 days.

(21) Appl. No.: 10/538,201

(22) PCT Filed: Dec. 9, 2003

(86) PCT No.: PCT/EP03/13960

§ 371 (c)(1),
(2), (4) Date: Mar. 8, 2006

(87) PCT Pub. No.: WO2004/052932

PCT Pub. Date: Jun. 24, 2004

(65) Prior Publication Data

US 2006/0183678 A1  Aug. 17, 2006

(30) Foreign Application Priority Data

Oct. 12, 2002 (GB) ................................ 0228832.2

(51) Int. Cl.
*C07K 16/00* (2006.01)
*A61K 39/395* (2006.01)
*A61K 39/00* (2006.01)

(52) U.S. Cl. .............. 424/141.1; 530/387.1; 530/388.1; 530/388.15; 530/387.9; 424/130.1

(58) Field of Classification Search ........................ None
See application file for complete search history.

(56) References Cited

FOREIGN PATENT DOCUMENTS

| EP | 1 174 441 | 1/2002 |
|---|---|---|
| RU | 2128226 C1 | 3/1999 |
| WO | WO-00/05364 A1 | 2/2000 |
| WO | WO00/31235 A2 | 6/2000 |
| WO | WO 01/51520 | 7/2001 |
| WO | WO 02/088306 | 11/2002 |
| WO | WO 03/004803 | 6/2003 |
| WO | WO-2004/052932 A2 | 6/2004 |

OTHER PUBLICATIONS

Chen, et al, 2000, Nature, 403: 434-439.*
Macallum, et al, J. Mol. Biol., 1996, 262: 732-745.*

Merkler Doron et al, "Locomotor Recovery in Spinal Cord-Injured Rats treated with an Antibody Neutralizing the Myelin-Associated Neurite Growth Inhibitor Nogo-A", Journal of neuroscience., vol. 21, No. 10, pp. 3665-3673, (2001.

Pot Caroline et al, "Nogo-A Expressed in Schwann Cells Impairs Axonal Regeneration After Peripheral Nerve Injury", Journal of Cell Biology, vol. 159, No. 1, pp. 29-35, (2002).

Raineteau O et al, "Improved Locomotor Recovery in Spinal Cord Injured Rats Treated with the Monoclonal Antibody IN-1", Society for Neuroscience Abstracts, vol. 27, No. 2, p. 1833, ((2001).

Li W. et al, ,, Neutralization of Myelin-Associated Nogo—A By A Nogo Receptor-Fc Fusion Protein, Society for Neuroscience Abstract Viewer and Itinerary Planner, vol. 2002 pages Abstract No. 333.2 & $32^{nd}$ Annual Meeting of the Society for Neuroscience (2002).

Choi e d et al, "Characterization of an Anti-Nogo Receptro FAB that Disrupts NOGOA/NOGO Receptor Interaction", Society for Neuroscience Abstract Viewer and Itinerary Planner, vol. 2002 pages Abstract No. 333.1 & $32^{nd}$ Annual Meeting of the Society for Neuroscience (2002).

Papadopoulos Catherine et al, "Functional Recovery and Neuroanatomical Plasticity Following Middle Cerebral Artery Occlusion and IN-1 Antibody Treatment in the Adult Rat", Annals of Neurology, vol. 51, No. 4, pp. 433-441 (2002).

Prinjha et al, "Characterisation and CNS Localisation of Nogo and the Nogo-Loop66 Receptor", Society for Neurosceince Abstracts, vol. 27, No. 1, p. 670 & $31^{st}$ Annual Meeting of the Society for Neuroscience San Diego, CA (2001).

Genbank Accession No. CAA77975, May 7, 1992.

Walter, Nik, (Nov. 24, 2003) "Schweizer Forscher heilen Verletzungen des Ruckenmarks bei Affen. Ein Traum wird ahr (Novartis erwahnt)" In the Media SonntagsZeitung.

Oertle et al. (Jul. 2, 2003) Nogo-A Inhibits Neurite Outgrowth and Cell Spreading with Three Discrete Regions. The Journal of Neurosciemce, 23(13):5393-5406.

Feidler et al. (2002) An Engineered IN-1 Fab fragment with improved affinity for the Nogo-A axonal growth inhibitor permits immunochemical detection and shows enhanced neutalizing activity. Protein Engineering 15(11):931-941.

Hunt et al. (2002) The Nogo receptor, its ligands and axonal regeneration in the spinal cord; A review. Journal of Neurocytology 31(2):93-120.

(Continued)

*Primary Examiner*—Dong Jiang
*Assistant Examiner*—Sandra Wegert
(74) *Attorney, Agent, or Firm*—Edwards Angell Palmer & Dodge LLP; Kathleen Williams; Amy DeCloux

(57) ABSTRACT

This invention relates to molecules, such as for example monoclonal antibodies or Fab fragments thereof, which are capable of binding to the human NogoA polypeptide or human NiG or human NiG- or human NogoA_623-640 with a dissociation constant <1000 nM; polynucleotides encoding such a binding molecule; an expression vector comprising such polynucleotides; the use of such a binding molecule in the treatment of nerve repair, a pharmaceutical composition comprising such a binding molecule; and to a method of treatment of diseases associated with nerve repair.

3 Claims, 1 Drawing Sheet

OTHER PUBLICATIONS

Oertle, Thomas, Molecular Characterisation of the reticulon family member Nogo. Doctoral THesis, Diss Naturwissenschaften ETH Zurich Nr. 14918 (http://e-collection.ethbib.ethz.ch/ecol-pool/diss/abstracts/p14918.pdf) record created Apr. 19, 2008, downloaded Mar. 6, 2009.

Caroni and Schwab, (1988) Two Membrane protein fractions from rat central myelin with inhibitory properties for neurite growth and fibroblast spreading. Neuron 106:1281-1288.

Zander et al.(2007) Epitope Mapping of the Neuronal Growth Inhibitor Nogo-A for the nogo receptor and the cognate antibody IN-1 by means of the SPOT technique. J. Molec. Recognition 20(3):185-96.

* cited by examiner

Figure 1:

```
human    TKVTEEVVANMPEGLTPDLVQEACESELNEVTGTKIAYETKMDLVQTSEVMQESLYPAAQ
monkey   GKVTEEVVANMPEGLTPDLVQEACESELNEVTGTKIAYETKMDLVQTSEVMQESLYPAAQ
rat      SKVTEAAVSNMPEGLTPDLVQEACESELNEATGTKIAYETKVDLVQTSEAIQESLYPTAQ
mouse    SKVTEAVVATMPEGLTPDLVQEACESELNEATGTKIAYETKVDLVQTSEAIQESIYPTAQ
         ****  .*:.******************.*********:*******..:***:**:**

human    LCPSFEESEATPSPVLPDIVMEAPLNSAVPSAGASVIQPSSSPLEASS-VNYESIKHEPE
monkey   LCPSFEESEATPSPVLPDIVMEAPLNSAVPSAGASAVQPSSSPLEASS-VNYESIIHEPE
rat      LCPSFEEAEATPSPVLPDIVMEAPLNSLLPSAGASVVQPSVSPLEAPPPVSYDSIKLEPE
mouse    LCPSFEEAEATPSPVLPDIVMEAPLNSLLPSTGASVAQPSASPLEVPSPVSYDGIKLEPE
         *****.**************.::*. * ****... *.*:.* *** human    NPPPYEEAMSVSLKKVSGIKEEIKEPENINAALQETEAPYISIACDLIKETKLSAEPAPD
monkey   NPPPYEEAMSVSLKKVSGIKEEIKEPESINAAVQETEAPYISIACDLIKETKLSAEPTPD
rat      NPPPYEEAMNVALKAL-GTKEGIKEPESFNAAVQETEAPYISIACDLIKETKLSTEPSPD
mouse    NPPPYEEAMSVALKTS-DSKEEIKEPESFNAAAQEAEAPYISIACDLIKETKLSTEPSPE
         *********.*:**  . ** *****.:*** **:******************.**.*:

human    FSDYSEMAKVEQPVPDHSELVEDSSPDSEPVDLFSDDSIPDVPQKQDETVMLVKESLTET
monkey   FSDYSEMAKVEQPVPDHSELVEDSSPDSEPVDLFSDDSIPDVPQKQDEAVMLVKENLPET
rat      FSNYSEIAKFEKSVPEHAELVEDSSPESEPVDLFSDDSIPEVPQTQEEAVMLMKESLTEV
mouse    FSNYSEIAKFEKSVPDHCELVDDSSPESEPVDLFSDDSIPEVPQTQEEAVMLMKESLTEV
         **:***:**:**.**:*.***:****:*****************.***.*:*:***.**.*.*.
```

ANTIBODY (11C7) ANTI NOGO A AND ITS PHARMACEUTICAL USE

This invention relates to NogoA binding molecules, such as for example monoclonal antibodies or Fab fragments thereof.

Neuronal regeneration following injury in the adult central nervous system (CNS) is limited due to the presence of the inhibitory myelin environment that ensheaths axons and formation of scar tissue. In the last few years important insights have been gained into the molecular understanding why the CNS is unable to spontaneously repair itself following injury. Inhibitory molecules in the myelin are the major impediment for the axonal regeneration, particularly immediately after the injury. So far NogoA, Myelin-Associated Glycoprotein (MAG) and myelin-oligodendrocyte glycoprotein (OMgp) have been characterised as potent inhibitors of neurite outgrowth. In addition, myelin also contains other inhibitory components, such as, chondroitin sulphate proteoglycans. Nogo-A is a member of the reticulon protein family and it has at least two biologically active and pharmacologically distinct domains termed Amino-Nogo and Nogo-66. While the receptor site for the former is not known so far, Nogo-66 inhibits neuronal growth In vitro and In vivo via the neuronal receptor NgR. In addition to Nogo-66, MAG and OMgp also bind to the NgR with high affinity and inhibit neurite outgrowth.

Potential new research approaches currently pursued for enhancement of nerve repair include digestion of scar tissue using an enzyme chondroitinase ABC, bridging techniques using Olfactory ensheathing cells and stem cells and protein growth factors to boost neuronal growth. Blocking actions of neurite outgrowth inhibitors by modulation of intracellular signalling mediators such as Rho, a membrane-bound guanosine trisphosphatase (GTPase), which appears to be a key link In the inhibition of axonal growth. Cyclic adenosine monophosphate (cAMP) which can overcome myelin associated inhibition in vitro and Induce regeneration in vivo. Use of peptide inhibitor of the NgR receptor (NEP 1-40) to induce neuronal regrowth and functional recovery in rats following spinal injury.

In addition to the use of the approaches described above, attention has also focused upon the use of certain monoclonal antibodies to neutralize neurite growth inhibitory molecules of the central and peripheral nervous system, In particular to neutralize the neurite growth inhibitory activity of NogoA. Thus it has been shown that the monoclonal antibody IN-1 or the IN-1 Fab fragment thereof induce neurite outgrowth in vitro and enhance sprouting and regeneration in vivo (Schwab M E et al. (1996) Physiol. Rev. 76, 319-370). Testing different domains of the NogoA for neurite growth inhibitory acitvity have delineated several inhibitory domains in the molecule (Chen et al. (2000) Nature 403, 434-439; GrandPre et a l. (2000) Nature 403, 439-444; Prinjha et al. (2000) Nature 403, 383-384; see also detailed analysis in Example 1).

Natural immunoglobulins or antibodies comprise a generally Y-shaped multimeric molecule having an antigen-binding site at the end of each upper arm. The remainder of the structure, in particular the stem of the Y mediates effector functions associated with the immunoglobulins. Antibodies consists of a 2 heavy and 2 light chains. Both heavy and light chains comprise a variable domain and a constant part. An antigen binding site consists of the variable domain of a heavy chain associated with the variable domain of a light chain. The variable domains of the heavy and light chains have the same general structure. More particularly, the antigen binding characteristics of an antibody are essentially determined by 3 specific regions in the variable domain of the heavy and light chains which are called hypervariable regions or complementarity determining regions (CDRs). These 3 hypervariable regions alternate with 4 framework regions (FRs) whose sequences are relatively conserved and which are not directly involved in binding. The CDRs form loops and are held in close proximity by the framework regions which largely adopt a β-sheet conformation. The CDRs of a heavy chain together with the CDRs of the associated light chain essentially constitute the antigen binding site of the antibody molecule. The determination as to what constitutes an FR or a CDR region is usually made by comparing the amino acid sequence of a number of antibodies raised in the same species. The general rules for identifying the CDR and FR regions are general knowledge of a man skilled in the art and can for example be found in the website ((www) bioinf.org.uk/abs/).

It has now surprisingly been found that a novel monoclonal mouse antibody (hereinafter called "11C7") raised against a polypeptide fragment of rat NogoA (SEQ ID NO: 1) and of the IgG1 type has better properties than the NogoA antibodies of the prior art especially with regard to the binding affinity to NogoA of different species including the homo sapiens and with regard to its higher NogoA neurite outgrowth neutralizing activity at a given antibody concentration. Moreover it is now possible to construct other NogoA binding molecules having the same hypervariable regions as the said antibody.

Accordingly, the invention provides binding molecules to a particular region or epitope of NogoA (hereinafter referred to as "the Binding Molecules of the invention" or simply "Binding Molecules"). Preferably the Binding Molecules of the invention bind to human NogoA_623-640 (orthologous fragment against which 11C7 was raised; =SEQ ID NO: 6), human Nig-D20 (orthologous to the smallest fragment of NogoA with neurite outgrowth inhibitory activity, SEQ ID NO: 24), human NogoA (SEQ ID NO: 5) or human NiG (which is the most potent neurite outgrowth inhibitory fragment of NogoA and starts at amino acid No. 186 and ends at amino acid No. 1004 of human NogoA, =SEQ ID NO: 5) with a dissociation constant (Kd)<1000 nM, more preferably with a Kd<100 nM, most preferably with a Kd<10 nM. The binding reaction may be shown by standard methods (qualitative assays) including, for example, the ELISA method described in Example 6 and the biosensor affinity method described in the example 7. In addition, the binding to human NogoA and almost more importantly the efficiency may be shown in a neurite outgrowth assay, e.g. as described below.

Thus, in a further preferred embodiment the Binding Molecules (at a concentration of 1 mg/ml, more preferably at 0.1 mg/ml even more preferably at 0.01 mg/ml culture medium) enhance the number of neurites of rat cerebellar granule cells on a substrate of rat spinal cord protein extract by at least 20%, preferably 50%, most preferred 100% compared to the number of neurites of rat cerebellar granule cells which are treated with a control antibody that does not bind to the human NogoA, human NiG, human Nig-D20 or NogoA_623-640 polypeptide (i.e. that has a dissociation constant>1000 nM).

In a further preferred embodiment the Binding Molecules of the invention comprises at least one antigen binding site, said antigen binding site comprising in sequence, the hypervariable regions CDR1-11C7, CDR2-11C7 and CDR3-11C7; said CDR1-11C7 having the amino acid sequence SEQ ID NO: 8, said CDR2-11C7 having the amino acid sequence SEQ ID NO: 9, and said CDR3-11C7 having the amino acid sequence SEQ ID NO: 10; and direct equivalents thereof.

In a further aspect of the invention, the Binding Molecule of the invention comprises at least one antigen binding site, said antigen binding site comprising either a) in sequence the hypervariable regions CDR1-11C7, CDR2-11C7 and CDR3-11C7; said CDR1-11C7 having the amino acid sequence of SEQ ID NO: 8, said CDR2-11C7 having the amino acid sequence of SEQ ID NO: 9, and said CDR3-11C7 having the amino acid sequence SEQ ID NO: 10; or b) in sequence the hypervariable regions CDR1'-11C7, CDR2'-11C7 and CDR3'-11C7, said CDR1'-11C7 having the amino acid sequence of SEQ ID NO: 11, said CDR2'-11C7 having the amino acid sequence of SEQ ID NO: 12, and said CDR3'-11C7 having the amino acid sequence of SEQ ID NO: 13; or c) direct equivalents thereof.

In a further aspect of the invention, the Binding Molecule of the invention comprises at least a) a first domain comprising in sequence the hypervariable regions CDR1-11C7, CDR2-11C7 and CDR3-11C7; said CDR1-11C7 having the amino acid sequence of SEQ ID NO: 8, said CDR2-11C7 having the amino acid sequence of SEQ ID NO: 9, and said CDR3-11C7 having the amino acid sequence SEQ ID NO: 10; and b) a second domain comprising in sequence the hypervariable regions CDR1'-11C7, CDR2'-11C7 and CDR3'-11C7, said CDR1'-11C7 having the amino acid sequence of SEQ ID NO: 11, said CDR2'-11C7 having the amino acid sequence of SEQ ID NO: 12, and said CDR3'-11C7 having the amino acid sequence of SEQ ID NO: 13; or c) direct equivalents thereof.

Moreover, the invention also provides the following Binding Molecule of the invention, which comprises at least one antigen binding site comprising a) either the variable part of the heavy chain of 11C7 (SEQ ID NO: 2); or b) the variable part of the light chain of 11C7 (SEQ ID NO: 3), or direct equivalents thereof.

When the antigen binding site comprises both the first and second domains, these may be located on the same polypeptide molecule or, preferably, each domain may be on a different chain, the first domain being part of an immunoglobulin heavy chain or fragment thereof and the second domain being part of an immunoglobulin light chain or fragment thereof.

Examples of Binding Molecules of the invention include antibodies as produced by B-cells or hybridomas and chimeric or humanized antibodies or any fragment thereof, e.g. F(ab')$_2$ and Fab fragments, as well as single chain or single domain antibodies.

A single chain antibody consists of the variable domains of an antibody heavy and light chains covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g. murine) origin. By "humanized antibody" is meant an antibody in which the hypervariable regions (CDRs) are of non-human (e.g. murine) origin, while all or substantially all the other parts of the immunoglobulin e.g. the constant regions and the highly conserved parts of the variable domains, i.e. the framework regions, are of human origin. A humanized antibody may however retain a few amino acids of the murine sequence in the parts of the framework regions adjacent to the hypervariable regions.

Hypervariable regions may be associated with any kind of framework regions, preferably of murine or human origin. Suitable framework regions are described in "Sequences of proteins of immunological Interest", Kabat E. A. et al, US department of health and human services, Public health service, National Institute of Health. Preferably the constant part of a human heavy chain of the Binding Molecules may be of the IgG4 type, including subtypes, preferably the constant part of a human light chain may be of the κ or λ type, more preferably of the κ type.

Monoclonal antibodies raised against a protein naturally found in all humans may be developed in a non-human system e.g. in mice. As a direct consequence of this, a xenogenic antibody as produced by a hybridoma, when administered to humans, elicits an undesirable immune response, which is predominantly mediated by the constant part of the xenogenic immunoglobulin. This clearly limits the use of such antibodies as they cannot be administered over a prolonged period of time. Therefore it is particularly preferred to use single chain, single domain, chimeric or humanized antibodies which are not likely to elicit a substantial allogenic response when administered to humans.

In view of the foregoing, a more preferred Binding Molecule of the invention is selected from a chimeric antibody, which comprises at least a) one immunoglobulin heavy chain or fragment thereof which comprises (i) a variable domain comprising in sequence the hypervariable regions CDR1-11C7, CDR2-11C7 and CDR3-11C7 and (ii) the constant part or fragment thereof of a human heavy chain; said CDR1-11C7 having the amino acid sequence (SEQ ID NO: 8), said CDR2-11C7 having the amino acid sequence (SEQ ID NO: 9), and said CDR3-11C7 having the amino acid sequence (SEQ ID NO: 10), and b) one immunoglobulin light chain or fragment thereof which comprises (i) a variable domain comprising in sequence the hypervariable regions CDR1'-11C7, CDR2'-11C7 and CDR3'-11C7 and (ii) the constant part or fragment thereof of a human light chain; said CDR1'-11C7 having the amino acid sequence (SEQ ID NO: 11), said CDR2'-11C7 having the amino acid sequence (SEQ ID NO: 12), and said CDR3'-11C7 having the amino acid sequence (SEQ ID NO: 13); or direct equivalents thereof.

Alternatively, a Binding Molecule of the invention may be selected from a single chain binding molecule which comprises an antigen binding site comprising a) a first domain comprising in sequence the hypervariable CDR1'-11C7, CDR2-11C7 and CDR3-11C7; said CDR1-11C7 having the amino acid sequence (SEQ ID NO: 8), said CDR2-11C7 having the amino acid sequence (SEQ ID NO: 9), and said CDR3-11C7 having the amino acid sequence (SEQ ID NO: 10); and b) a second domain comprising in sequence the hypervariable CDR1'-11C7, CDR2'-11C7 and CDR3'-11C7; said CDR1'-11C7 having the amino acid sequence (SEQ ID NO: 11), said CDR2'-11C7 having the amino acid sequence (SEQ ID NO: 12), and said CDR3'-11C7 having the amino acid sequence (SEQ ID NO: 13); and c) a peptide linker which is bound either to the N-terminal extremity of the first domain and to the C-terminal extremity of the second domain or to the C-terminal extremity of the first domain and to the N-terminal extremity of second domain;

or direct equivalents thereof.

As it is well known, minor changes in an amino acid sequence such as deletion, addition or substitution of one or several amino acids may lead to an allelic form of the original protein which has substantially identical properties. Thus, by the term "direct equivalents thereof" is meant either any single domain Binding Molecule of the invention (molecule X)

(i) in which each of the hypervariable regions CDR1, CDR2, and CDR3 of the Binding Molecule is at least 50 or 80% homologous, preferably at least 90% homologous, more preferably at least 95, 96, 97, 98, 99% homologous to the equivalent hypervariable regions of CDR1-11C7 (SEQ ID NO: 8), CDR2-11C7 (SEQ ID NO: 9) and CDR3-11C7 (SEQ ID NO: 10), whereas CDR1 is equivalent to CDR1-11C7, CDR2 is equivalent to CDR2-11C7, CDR3 is equivalent to CDR3-11C7; and (ii) which is capable of binding to the human NogoA, human NiG, human NiG-D20, or human NogoA_623-640, preferably with a dissociation constant (Kd)<1000 nM, more preferably with a Kd<100 nM, most preferably with a Kd<10 nM, or any binding molecule of the invention having at least two domains per binding site (molecule X')

(iii) in which each of the hypervariable regions CDR1, CDR2, CDR3, CDR1', CDR2' and CDR3' is at least 50 or 80% homologous, preferably at least 90% homologous, more preferably at least 95, 96, 97, 98, 99% identical to the equivalent hypervariable regions of CDR1-11C7 (SEQ ID NO: 8), CDR2-11C7 (SEQ ID NO: 9), CDR3-11C7 (SEQ ID NO: 10), CDR1'-11C7 (SEQ ID NO: 11), CDR2'-11C7 (SEQ ID NO: 12), and CDR3'-11C7 (SEQ ID NO: 13), whereas CDR1 is equivalent to CDR1-11C7, CDR2 is equivalent to CDR2-11C7, CDR3 is equivalent to CDR3-11C7, CDR1' is equivalent to CDR1'-11C7, CDR2' is equivalent to CDR2'-11C7, CDR3' is equivalent to CDR3'-11C7; and (iv) which is capable of binding the human NogoA, human NiG, human NiG-D20, or human NogoA_623-640, preferably with a dissociation constant (Kd)<1000 nM, more preferably with a Kd<100 nM, most preferably with a Kd<10 nM.

Thus further embodiments of the inventions are for example a Binding Molecule which is capable of binding to the human NogoA, human NiG, human NiG-D20, or human NogoA_623-640 with a dissociation constant <1000 nM and comprises at least one antigen binding site, said antigen binding site comprising either in sequence the hypervariable regions CDR1, CDR2, and CDR3, of which each of the hypervariable regions are at least 50%, preferably 80, 90, 95, 96, 97, 98, 99% homologous to their equivalent hypervariable regions CDR1-11C7 (SEQ ID NO: 8), CDR2-11C7 (SEQ ID NO: 9) and CDR3-11C7 (SEQ ID NO: 10); or in sequence the hypervariable regions CDR1', CDR2', and CDR3', of which each of the hypervariable regions are at least 50%, preferably 80, 90, 95, 96, 97, 98, 99% homologous to their equivalent hypervariable regions CDR1'-11C7 (SEQ ID NO: 11), CDR2'-11C7 (SEQ ID NO: 12) and CDR3'-11C7 (SEQ ID NO: 13).

Furthermore, a Binding Molecule which is capable of binding the human NogoA, human NiG, human NiG-D20, or human NogoA_623-640 with a dissociation constant <1000 nM and comprises a first antigen binding site comprising in sequence the hypervariable regions CDR1, CDR2, and CDR3, of which each of the hypervariable regions are at least 50%, preferably 80, 90, 95, 96, 97, 98, 99% homologous to their equivalent hypervariable regions CDR1-11C7 (SEQ ID NO: 8), CDR2-11C7 (SEQ ID NO: 9) and CDR3-11C7 (SEQ ID NO: 10); and a second antigen binding site comprising in sequence the hypervariable regions CDR1', CDR2', and CDR3', of which each of the hypervariable regions are at least 50%, preferably 80, 90, 95, 96, 97, 98, 99% homologous to their equivaleht hypervariable regions CDR1'-11C7 (SEQ ID NO: 11), CDR2'-11C7 (SEQ ID NO: 12) and CDR3'-11C7 (SEQ ID NO: 13).

This dissociation constant may be conveniently tested in various assays including, for example, the biosensor affinity method described in the example 7. In addition, the binding and functional effect of the Binding Molecules may be shown in a bioassay, e.g. as described below.

The constant part of a human heavy chain may be of the $\gamma 1$; $\gamma 2$; $\gamma 3$; $\gamma 4$; $\alpha 1$; $\alpha 2$; $\delta$ or $\epsilon$ type, preferably of the $\gamma$ type, more preferably of the $\gamma 4$; type, whereas the constant part of a human light chain may be of the $\kappa$ or $\lambda$ type (which includes the $\lambda 1$; $\lambda 2$; and $\lambda 3$ subtypes) but is preferably of the $\kappa$ type. The amino acid sequence of all these constant parts are given in Kabat et al (Supra).

Conjugates of the binding molecules of the invention, e.g. enzyme or toxin or radioisotope conjugates, are also included within the scope of the invention.

"Polypeptide", if not otherwise specified herein, includes any peptide or protein comprising amino acids joined to each other by peptide bonds, having an amino acid sequence starting at the N-terminal extremity and ending at the C-terminal extremity. Preferably the polypeptide of the present invention is a monoclonal antibody, more preferred is a chimeric (also called V-grafted) or humanised (also called CDR-grafted) monoclonal antibody. The humanised (CDR-grafted) monoclonal antibody may or may not include further mutations introduced into the framework (FR) sequences of the acceptor antibody.

A functional derivative of a polypeptide as used herein includes a molecule having a qualitative biological activity in common with a polypeptide to the present invention, i.e. having the ability to bind to the human NogoA, human NiG, human NiG-D20, or human NogoA_623-640. A functional derivative includes fragments and peptide analogs of a polpypeptide according to the present invention. Fragments comprise regions within the sequence of a polypeptide according to the present invention, e.g. of a specified sequence. The term "derivative" is used to define amino acid sequence variants, and covalent modifications of a polypeptide according to the present invention. e.g. of a specified sequence. The functional derivatives of a polypeptide according to the present invention, e.g. of a specified sequence, e.g. of the hypervariable region of the light and the heavy chain, preferably have at least about 65%, more preferably at least about 75%, even more preferably at least about 85%, most preferably at least about 95, 96, 97, 98, 99% overall sequence homology with the amino acid sequence of a polypeptide according to the present invention, e.g. of a specified sequence, and substantially retain the ability to bind the human NogoA, human NiG, human NiG-D20, or human NogoA_623-640.

The term "covalent modification" includes modifications of a polypeptide according to the present invention, e.g. of a specified sequence; or a fragment thereof with an organic proteinaceous or non-proteinaceous derivatizing agent, fusions to heterologous polypeptide sequences, and post-translational modifications. Covalent modified polypeptides, e.g. of a specified sequence, still have the ability bind to the human NogoA, human NiG, human NiG-D20, or human NogoA_623-640 by crosslinking. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains, see e.g. T. E. Creighton, Proteins: Structure and Molecular Properties, W. H. Freeman & Co., San Francisco, pp. 79-86 (1983). Covalent modifications e.g. include fusion proteins comprising a polypeptide according to the present invention, e.g. of a specified sequence and their amino acid sequence variants, such as immunoadhesins, and N-terminal fusions to heterologous signal sequences.

"Homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or Cterminal extensions nor insertions shall be construed as reducing identity or homology. Methods and computer programs for the alignment are well known.

"Amino acid(s)" refer to all naturally occurring L-α-amino acids, e.g. and including D-amino acids. The amino acids are identified by either the well known single-letter or three-letter desigriations.

The term "amino acid sequence variant" refers to molecules with some differences in their amino acid sequences as compared to a polypeptide according to the present invention, e.g. of a specified sequence. Amino acid sequence variants of a polypeptide according to the present invention, e.g. of a specified sequence, still have the ability to bind to human NogoA or human NiG or more preferably to NogoA_623-640. Substitutional variants are those that have at least one amino acid residue removed and a different amino acid inserted in its place at the same position in a polypeptide according to the present invention, e.g. of a specified sequence. These substitutions may be single, where only one amino acid in the molecule has been substituted, or they may be multiple, where two or more amino acids have been substituted in the same molecule. Insertional variants are those with one or more amino acids inserted immediately adjacent to an amino acid at a particular position in a polypeptide according to the present invention, e.g. of a specified sequence. Immediately adjacent to an amino acid means connected to either the α-carboxy or α-amino functional group of the amino acid. Deletional variants are those with one or more amino acids in a polypeptide according to the present invention, e.g. of a specified sequence, removed. Ordinarily, deletional variants will have one or two amino acids deleted in a particular region of the molecule.

A binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided
(i) DNA molecules encoding a single domain Binding Molecule of the invention, a single chain Binding Molecule of the invention, a heavy or light chain or fragments thereof of a Binding Molecule of the invention; and
(ii) the use of the DNA molecules of the invention for the production of a Binding Molecule of the invention by recombinant means.

The present state of the art is such that the skilled man will be able to synthesize the DNA molecules of the invention given the information provided herein i.e. the amino acid sequences of the hypervariable regions and the DNA sequences coding for them. A method for constructing a variable domain gene is for example described in EP 239 400 and may be briefly summarized as follows: A gene encoding a variable domain of a monoclonal antibody of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences given CDR1-11C7, CDR2-11C7, CDR3-11C7, CDR1'-11C7, CDR2'-11C7 and CDR3'-11C7 above. These cassettes are provided with sticky ends so that they can be ligated at the junctions to the framework by standard protocol for achieving a DNA molecule encoding an immunoglobulin variable domain.

Furthermore, it is not necessary to have access to the mRNA from a producing hybridoma cell line in order to obtain a DNA construct coding for the monoclonal antibodies of the invention. Thus PCT application WO 90/07861 gives full instructions for the production of a monoclonal antibody by recombinant DNA techniques given only written information as to the nucleotide sequence of the gene.

The method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector.

DNA molecules encoding single chain antibodies may also be prepared by standard methods, for example, as described in WO 88/1649.

In a particular embodiment of the invention, the recombinant means for the production of some of the Binding Molecules of the invention includes first and second DNA constructs as described below:

The first DNA construct encodes a heavy chain or fragment thereof and comprises
a) a first part which encodes a variable domain comprising alternatively framework and hypervariable regions, said hypervariable regions comprising in sequence DNA- CDR1-11C7 (SEQ ID NO: 15), DNA-CDR2-11C7 (SEQ ID NO: 16) and DNA-CDR3-11C7 (SEQ ID NO: 17); this first part starting with a codon encoding the first amino acid of the variable domain and ending with a codon encoding the last amino acid of the variable domain, and b) a second part encoding a heavy chain constant part or fragment thereof which starts with a codon encoding the first amino acid of the constant part of the heavy chain and ends with a codon encoding the last amino acid of the constant part or fragment thereof, followed by a non-sense codon.

Preferably, the second part encodes the constant part of a human heavy chain, more preferably the constant part of the human γ4 chain. This second part may be a DNA fragment of genomic origin (comprising introns) or a cDNA fragment (without introns).

The second DNA construct encodes a light chain or fragment thereof and comprises a) a first part which encodes a variable domain comprising alternatively framework and hypervariable regions; said hypervariable regions comprising in sequence DNA-CDR1'-11C7 (SEQ ID NO: 17), DNA-CDR2'-11C7 (SEQ ID NO: 18) and DNA-CDR3'-11C7 (SEQ ID NO: 19), this first part starting with a codon encoding the first amino acid of the variable domain and ending with a codon encoding the last amino acid of the variable domain, and b) a second part encoding a light chain constant part or fragment thereof which starts with a codon encoding the first amino acid of the constant part of the light chain and ends with a codon encoding the last amino acid of the constant part or fragment thereof followed by a non-sense codon.

Preferably, the second part encodes the constant part of a human light chain, more preferably the constant part of the human κ chain.

The first or second DNA construct advantageously comprises a third part which is located upstream of the first part and which encodes part of a leader peptide; this third part starting with the codon encoding the first amino acid and ending with the last amino acid of the leader peptide. This peptide is required for secretion of the chains by the host organism in which they are expressed and is subsequently removed by the host organism. Preferably, the third part of the first DNA construct encodes a leader peptide having an amino acid sequence substantially identical to the amino acid sequence of the heavy chain leader sequence as shown in SEQ ID NO: 21 (starting with the amino acid at position −19 and ending with the amino acid at position −1). Also preferably, the third part of the second DNA construct encodes a leader peptide having an amino acid sequence as shown in SEQ ID NO: 23 (light chain, starting with the amino acid at position −18 and ending with the amino acid at position −1).

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, it is particularly preferred to use the promoter of an immunoglobulin gene.

The desired antibody may be produced in a cell culture or in a transgenic animal. A suitable transgenic animal may be obtained according to standard methods which include micro injecting into eggs the first and second DNA constructs placed under suitable control sequences transferring the so prepared eggs into appropriate pseudo-pregnant females and selecting a descendant expressing the desired antibody.

When the antibody chains have to be produced in a cell culture, the DNA constructs must first be inserted into either a single expression vector or into two separate but compatible expression vectors, the latter possibility being preferred.

Accordingly, the invention also provides an expression vector able to replicate in a prokaryotic or eukaryotic cell line which comprises at least one of the DNA constructs above described.

Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin e.g. a myeloma, hybridoma or a normal immortalized B-cell, but does not express any endogeneous antibody heavy or light chain.

It is also preferred that the host organism contains a large number of copies of the vectors per cell. If the host organism is a mammalian cell line, this desirable goal may be reached by amplifying the number of copies according to standard methods. Amplification methods usually consist of selecting for increased resistance to a drug, said resistance being encoded by the expression vector.

In another aspect of the invention, there is provided a process for producing a multi-chain binding molecule of the invention, which comprises (i) culturing an organism which is transformed with the first and second DNA constructs of the invention and (ii) recovering an active binding molecule of the invention from the culture.

Alternatively, the heavy and light chains may be separately recovered and reconstituted into an active binding molecule after in vitro refolding. Reconstitution methods are well-known in the art; Examples of methods are in particular provided in EP 120 674 or in EP 125 023.

Therefore a process may also comprise (i) culturing a first organism which is transformed with a first DNA construct of the invention and recovering said heavy chain or fragment thereof from the culture and (ii) culturing a second organism which is transformed with a second DNA construct of the invention and recovering said light chain or fragment thereof from the culture and (iii) reconstituting in vitro an active binding molecule of the invention from the heavy chain or fragment thereof obtained in (i) and the light chain or fragment thereof obtained in (ii).

In a similar manner, there is also provided a process for producing a single chain or single domain binding molecule of the invention which comprises (i) culturing an organism which is transformed with a DNA construct respectively encoding a single chain or single domain binding molecule of the invention and (ii) recovering said molecule from the culture.

The binding molecules of the invention exhibit very good nerve repair activity as shown, for example, in the granule cell neurite outgrowth model.

1. Granule Cell Neurite Outgrowth Assay (in vitro)

Neurite outgrowth from dissociated cerebellar granule cells are determined as described (Niederöst et al. (1999) J. Neurosci. 19: 8979-8989). Briefly, cerebella are removed from decapitated postnatal day 5-7 rats and dissociated by trypsin treatment. To reduce fibroblast contamination, the cells are preplated onto bacterial dishes. 75'000 cells are then cultured per well in 4-well Greiner tissue culture (Huber & Co AG, Rheinach, Basel) dishes (well surface: 1 cm2) in medium (Neurobasal with B27 serum replacement, Invitrogen). Culture dishes are coated with poly-L-lysine (Sigma). Chaps extracted proteins from total spinal cord homogenates of adult rats (Spillmann et al. (1998) J. Biol. Chem. 273: 19283-19293) is coated at protein concentrations of 0.5 till 8 µg per well over night at 4° C. and washed. The binding molecules of the invention are then pre-incubated for 30 min on the test substrate and removed before the cells are added. Cerebellar granule cells are added and incubated for 24 hours. To stop the experiment, 2 ml of 4% buffered formaldehyde is slowly added to the culture dishes. Cultures are then stained by immunofluorescence for the growth-associated protein GAP-43 and with Hoechst for cell nuclei (Granule cells are stained with Hoechst in order to see if all the cells have neurites (neurite visualised with anti-GAP-43)). Three pictures are taken randomly at a defined distance of the upper, lower and lateral edge of each well with a 40× objectif on a Zeiss Axiophot Fluorescence Microscope. All the neurites in a field are counted on number-coded, randomly arranged photographs. The response (outgrowth of the granule cell neurites) is dose-dependent in the range of about 0.1-10 µg total protein per well (the specific activities of a given preparation vary within this range).

Enhancement of neurite outgrowth of cerebellar granule cell in the non-permissive environment of the above prepared spinal cord extract by preincubation with a binding molecule of the invention may be observed. E.g. a typical profile for the neutralizing effect of the mouse 11C7-IgG1 antibody in the granule cell neurite outgrowth model is given below:

| Assay 1: | | |
|---|---|---|
| rat myelin coated at 1 µg per well | Neurites per field | Percentage |
| no antibody | 80.5 | 100% |
| +mouse IgG | 86.5 | 108% |
| 11C7 250 µg/ml | 160 | 199% |

| Assay 2: | | |
|---|---|---|
| rat myelin (prep. 2) coated at 8 µg per well | Neurites per field | Percentage |
| no antibody | 20 | 100% |
| +mouse IgG | 17.3 | 86.5% |
| 11C7 250 µg/ml | 31 | 155% |
| 11C7 75 µg/ml | 26 | 130% |
| 11C7 7.5 µg/ml | 26 | 130% |

The neutralizing activity of the molecules of the invention may also be estimated by measuring the regenerative sprouting and neurite outgrowth in the in vivo spinal cord injury model as follows:

2. Spinal Cord Injury Model (in vivo)

Adult Lewis rats are injured microsurgically by transecting the dorsal half of the spinal cord bilaterally at the level of the 8$^{th}$ thoracic vertebra. Laminectomy, anesthesia and surgery are described in Schnell and Schwab 1993 (Eur. J. Neurosci. 5: 1156-1171). Controls or binding molecules of the invention are applied in two different ways: either by implanting $10^6$ freshly harvested hybridoma cells into one side of the cerebral cortex (grafted animals) or, alternatively, by an implanted intraventricular canula linked to a subcutaneously implanted 2 ml Alzet (Alza Corporation, Palo Alto) pump (pump animals).—Hybridoma grafted animals: Rats are immunosuppressed for 7-10 days with cyclosporin A and sacrificed by transcardial perfusion with 4% buffered formalin 14 days after injury.—Pump animals: Binding molecules of the invention (e.g. at 3.3 mg/ml for mouse 11C7) are filled into 2 ml pumps delivering 0.5 µl/h into the lateral ventricle for 2 weeks. Pumps are implanted at the time of the spinal cord lesion, and rats are sacrificed 2 weeks later.

Neuroanatomical tracing: The motor and sensory corticospinal tract is traced by injecting the anterograde tracer biotin dextran amine (BDA) into the cortex of the side opposite to the pump or the graft. BDA is transported to the spinal cord within 10-14 days and visualized using diaminobenzidine (DAB) as a substrate as described in Brösamle et al., (2000 J. Neurosci. 20: 8061-8068).

Evalutation of anatomical resufts: Two methods of evaluation are used: a semi-quantitative and a quantitative one. Semi-quantitative estimation of intensity of sprouting and regeneration: Complete sagittal section series of number-coded, randomly mixed animals are evaluated for the presence and density of regenerating sprouts rostral to the lesion using the following definitions: regenerative sprouts are fibers emanating from the transected CST; they are long, irregular in their course, much less branched than the normal grey matter collaterals, and they growth towards and ventrally or laterally around the lesion. Regenerative sprouts often end in a growth cone which can be small and bulbouse or large and branched. Density of sprouting is rated on a scale of 0-3 for each animal.—Long distance regeneration: fibers that can be followed through the lesion into the caudal spinal cord are considered long-distance regenerating fibers. Their maximal distance from the lesion site can be measured, but is often a minimal distance as some unlesioned fibers from the small ventral funiculus CST are often present; their branches mix with those of regenerating axons and make distinction difficult.

Fiber counts (quantitative assay): A line positioned at −0.5 mm rostral to the end of the transected CST is posed on alternating sections of the grey matter, and all intersections with CST fibers (normal collaterals or sprouts) are counted. Similar lines are positioned caudal to the lesion at a distance of +0.5, +2 and +5 mm from the lesion center. Intersecting fibers are counted and the 3 levels are added to a sum reflecting CST fibers in the caudal spinal cord. These caudal fibers are divided by the number of fibers −0.5 mm rostral to the CST end to obtain a ratio.

Two weeks after a spinal cord injury destroying about 40% of the spinal cord segment T8, mainly in the dorsal half, including both main CSTs: tracing of the CST in control animals show a moderate degree of reactive sprouting of the tract. This phenomenon corresponds to the spontaneous sprouting in response to injury well known in the literature. Injured rats being treated with the binding molecules of the invention or with pumps delivering the binding molecules of the invention may show an enhanced sprouting at the lesion site and regeneration of damaged axons neurite outgrowth of damaged neurites.

Therefore the invention also provides (i) the use of the binding molecules of the invention in the nerve repair of a mammalian nervous system, in particular human nervous system, (ii) a method of repairing nerves of a mammalian nervous system, in particular human nervous system which comprises administering an effective amount of the binding molecules of the invention to a patient in need of such treatment, or (iii) a pharmaceutical composition for nerve repair of a mammalian nervous system, in particular human nervous system which comprises the binding molecules of the invention and a pharmaceutically acceptable carrier or diluent.

In particular, the binding molecules of the invention are useful for axonal regeneration and improved sprouting after nerve fiber damage. Thus the molecules of the invention have a wide utility in particular for human subjects. For example the binding molecule of the invention are useful in the treatment of various diseases of the peripheral (PNS) and central (CNS) nervous system, i.e. more particularly in neurodegenerative diseases such as Alzheimer disease, Parkinson disease, Amyotrophic lateral sclerosis (ALS), Lewy like pathologies or other dementia in general, diseases following cranial, cerebral or spinal trauma, stroke or a demyeliating disease. Such demyelinating diseases include, but are not limited to, multiple sclerosis, monophasic demyelination, encephalomyelitis, multifocal leukoencephalopathy, panencephalitis, Marchiafava-Bignami disease, pontine myelmolysis, adrenoleukodystrophy, Pelizaeus-Merzbacher disease, Spongy degeneration, Alexander's disease, Canavan's disease, metachromatic leukodystrophy and Krabbe's disease. In one example, administration of the binding molecules of the invention can be used to treat a demyelinating disease associated with NogoA protein. In another example, cells which express the binding molecules of the invention may be transplanted to a site spinal cord injury to facilitate axonal growth throughout the injured site. Such transplanted cells would provide a means for restoring spinal cord function following injury or trauma. Such cells could include olfactory ensheathing cells and stem cells of different lineages of fetal nerve or tissue grafts.

In addition, the Binding Molecules of the invention are useful for the treatment of degenerative ocular disorders which may directly or indirectly involve the degeneration of retinal or corneal cells including ischemic retinopathies in general, anterior ischemic optic neuropathy, all forms of optic neuritis, age-related macular degeneration, diabetic retinopathy, cystoid macular edema (CME), retinitis pigmentosa, Stargardt's disease, Best's vitelliform retinal degeneration, Leber's congenital amaurosis and other hereditary retinal degenerations, pathologic myopia, retinopathy of prematurity, and Leber's hereditary optic neuropathy, the after effects of corneal transplantation or of refractive corneal surgery, and herpes keratitis.

Furthermore, it was shown that NogoA plays a role in psychiatric conditions, in particular schizophrenia and depression. Hence, the binding molecules of the invention are useful for the treatment of psychiatric conditions, in particular schizophrenia and depression.

The Binding Molecules of the invention can be provided alone, or in combination, or in sequential combination with other agents. For example, the binding molecules of the invention can be administered in combination with anti-inflammatory agents such as but not limited to corticosteroids following stroke or spinal cord injury as a means for blocking further neuronal damage and inhibition of axonal regeneration, Neurotrophic factors such as NGF, BDNF or other drugs for neurodegenerative diseases such as Exelon™ or Levodopa. As used herein, two agents are said to be administered in combination when the two agents are administered simultaneously or are administered independently in a fashion such that the agents will act at the same time.

For the treatment of psychiatric conditions, in particular schizophrenia or depression, the Binding Molecules of the invention can be provided alone or in combination in particular with other agents selected from the group consisting of (a) anti-epileptic drugs selected from barbiturates and derivatives thereof, benzodiazepines, carboxamides, hydantoins, succinimides, valproic acid and other fatty acid derivates and other anti-epileptic drugs, (b) conventional antipsychotics, (c) atypical antipsychotics and (d) antidepressants.

The term "barbiturates and derivatives thereof" as used herein includes, but is not limited to Phenobarbital and primidon. The term "benzodiazepines" as used herein includes, but is not limited to clonazepam, diazepam and lorazepam. The term "carboxamides" as used herein includes, but is not limited to carbamazepine, oxcarbazepine and 10-hydroxy-10, 11-dihydrocarbamazepine. The term "hydantoins" as used herein includes, but is not limited to phenyloin. The term "succinimides" as used herein includes, but is not limited to ethosuximide and rriesuximide. The term "valproic acid and other fatty acid derivates" as used herein includes, but is not limited to valproic acid sodium salt, tiagabine hydrochloride monohydrate and vigrabatrine. The term "other anti-epileptic drugs" as used herein includes, but is not limited to levetiracetam, lamotrigine, gabapentin and felbamate.

The term "conventional antipsychotics" as used herein includes, but is not limited to haloperidol and fluphenazine.

The term "atypical antipsychotics" as used herein relates to clozaril, risperidone, olanzapine, quetiapine, ziprasidone and aripiprazol.

The term "antidepressants" as used herein includes, but is not limited to selective serotonin reuptake inhibitors (SSRI's), or selective serotonin and norepinephrine reuptake inhibitors (SNRI-s). An SSRI's suitable for the present invention can be selected from fluoxetine, fuvoxamine, sertraline, paroxetine, citalopram and escitalopram.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

For the indications mentioned above, the appropriate dosage will, of course, vary depending upon, for example, the particular molecule of the invention to be employed, the mode of administration and the nature and severity of the condition being treated. The Binding Molecules of the invention are conveniently administered by pumps or injected as therapeutics at the lesioned site, e.g. they can be administered directly into the CNS intracranially or into the spine intrathecally to the lesioned site.

Pharmaceutical compositions of the invention may be manufactured in conventional manner. E.g. a composition according to the invention comprising the molecules of the invention is preferably provided in lyophilized form. For immediate administration it is dissolved in a suitable aqueous carrier, for example sterile water for injection or sterile buffered physiological saline.

To aid in making up suitable compositions, the binding molecules of the invention and optionally a second drug enhancing the effect of the Binding Molecules of the invention, may be packaged separately within the same container, with instructions for mixing or concomitant administration. Optional second drug candidates are provided above.

The synergistic effect of a combination of the binding molecules of the invention and growth factors such as NGF may be demonstrated in vivo by the spinal cord injury model described above.

BRIEF DESCRIPTION OF THE DRAWING

FIG. 1: Sequence Comparison: Sequence comparison of the NiG from different species, human, monkey, rat and mouse (SEQ ID NO:45, SEQ ID NO:46, SEQ ID NO:47 and SEQ ID NO:48, respectively), showing the immunogenic peptide sequence for the 11C7 mAb.

The invention will be more fully understood by reference to the following examples. They should not, however, be construed as limiting the scope of the invention.

In the following examples all temperatures are in degree Celsius (° C.).

The monoclonal antibody of attention in the Examples is a Binding Molecule according to the present invention comprising the variable part of the light chain (SEQ ID NO: 3) and the variable part of the heavy chain (SEQ ID NO: 2).

The following abbreviations are used:
ELISA enzyme linked immuno-sorbant assay
FACS fluorescence activated cell sorting.
FITC fluorescein isothiocyanate
FBS foetal bovine serum
HCMV human cytomegalovirus promoter
IgG immunoglobulin isotype G
MAb monoclonal antibody
PBS phosphate-buffered saline
PCR polymerase chain reaction

EXAMPLE 1

NiG-D20 (SEQ ID NO: 24) is One of the Neurite Outgrowth Inhibitory Fragments of NogoA Methods:

a) Rat Nogo-A deletion library: Deletion constructs are made using internal restriction sites, by ExonucleaseIII/Mung Bean Nuclease treatment and by PCR with rat Nogo-A-specific primers on rat Nogo-(method as in WO00/31235): rat Nogo-A (aa 1-1163; DNA as shown hereafter related to the amino acids of rat NogoA (SEQ ID NO: 26), e.g. aa 1-1163 means that the cDNA construct encodes for polypeptide which starts at the amino acid1 and ends at amino acid 1163 of the rat polypeptide sequence of NogoA), rat Nogo-B (aa 1-172+976-1163), rat Nogo-C (Nogo-C N-terminal 11 aa+aa 976-1163), rat Nogo-66 (aa 1019-1083), rat GST-Nogo-66 (aa 1026-1091), rat NIR-G (aa 1-979), rat NiR (1-172), rat NiR-D1 (aa 1-31), rat NiR-D2 (aa 59-172), rat NiR-D3 (aa 1-31+59-172), rat EST-Nogo1 (aa 762-1163), rat NiG (aa 174-979), rat NiG-D1 (aa174-909), rat NiG-D2 (aa 174-865), rat NiG-D3 (aa 172-723), rat NiG-D4 (aa 172-646), rat NiG-D5 (aa 293-647), rat NiG-D6 (aa 763-975), rat NiG-D7 (aa 174-235+294-979), rat NiG-D8 (aa 218-653), rat NiG-D9 (aa 172-259+646-974), rat NiG-D10 (aa 293-979), rat NiG-D11 (aa 209-268), rat NiG-D12 (aa 198-233), rat NIG-D13 (aa 174-216), rat NiG-D14 (aa 174-260), rat NiG-D15 (aa 174-190+493-979), rat NiG-D16 (aa 174-190+621-979), rat NiG-D17 (aa 174-190+259-979), rat NiG-D18 (aa 174-190+263-979), rat NiG-D19 (aa 763-865), rat NiG-D20 (aa 544-725), rat NiG-D21 (aa 812-918), rat NiG-D22 (aa 866-975), rat NiG-D23 (aa 914-975), rat NiG-D24 (aa 544-685), rat NiG-D25 (aa 614-725), rat NiG-D26 (aa 544-613), rat NiG-D27 (aa 581-648), rat NiG-D28 (aa 614-685), rat NiG-D29 (aa 648-725), rat NiG-D30 (aa 682-725), rat NiG-D31 (aa 544-580), rat NiG-D32 (aa 581-613), rat NiG-D33 (aa 614-648), rat NiG-D34 (aa 648-685), rat NiG-D35 (aa 260-556), rat NiG-D36 (aa 260-415). NiR-G and NiR-a are derived from Nogo-A-pET28 by restriction enzyme digestions. NiG is derived from NiR-G by restriction digestion and MungBean Nuclease treatment. NiG-D1, -D3, -D4, -D5, -D7, -D8, -D9, -D10 derived from NiG-pET28 by restriction enzyme digestions. NiG-D15, -D16, -D17, -D18 derived from NiGp-ET28 by Exonuclease III digestion. NiR-b, NiR-D1, -D2, -D3 derived by PCR with NiR-apET28 as a template. NiG-D2, -D6, -D11, -D12, -D13, -D14, -D19, -D20, -D21, -D22, -D23, -D24, -D25, -D26, -D27, -D28, -D29, -D30, -D31, -D32, -D33, -D34, -D35, -D36 derived by PCR using NiG-pET28 as a template. All constructs subcloned into pET28. pET28 used for all the constructs mentioned aboved. pGEX-6P used for GST-Nogo66 and pET26 for periplasmic expression of rat NiG. Human GST-Nogo-66 (aa 1055-1120 of human Nogo-A) is cloned by PCR on human NogoA DNA (SEQ ID NO: 4) as a template. Deletion constructs are then cloned into pET28 vector (Novagen), pGEX-6P (Amersham Pharmacia Biotech) and pET26 vector (Novagen). Human GST-Nogo-66 corresponds to the GST-nogo protein published by GrandPré et al. (supra). Synthetic rat peptide 4 EELVQKYSNSALGH-VNSTIKELRRL (SEQ ID NO: 27) corresponds to the human peptide 4 (Human peptide 4 has been shown to be the inhibitory region of the Nogo-66 domain (GrandPré et al., 2000)). The orthologous rat peptide has a single mismatch C->S (see peptide 4 sequence in GrandPré et al., 2000, supra). Synthetic Pro/Ser-rich peptide PSSPPPSSPPPSSPPPS (SEQ ID NO: 28) as well as rat peptide 4 have been produced and HPLC-purified by Primm S A. Human NogoA_623-640 (SEQ ID NO: 6) is synthesised and purified by Research Genetics Inc.

b) Generation of human Nogo-A expression constructs (pRK7-hNogo-A): A human cDNA library constructed in lambda gt10 (Clontech) is screened with duplicate filter sets using standard procedures. Fragments of human Nogo-A are amplified by PCR from human whole brain cDNA (Clontech) using a standard protocol and subsequently cloned into pBluescript, digested and isolated, or used as screening probes directly. A 400 bp XhoI/SmaI fragment is used as 5' probe, the 3' probe is amplified with primers CA-NA-2F: 5'-AAG CAC CAT TGA ATT CTG CAG TTC C-3' (SEQ ID NO: 29) and CA-NA-3R: 5'-AAC TGC AGT ACT GAG CTC CTC CAT CTG C-3' (SEQ ID NO: 30). Positive clones are isolated, subcloned and sequence confirmed. To obtain a full length human Nogo-A cDNA, overlapping clones are assembled using an unique EcoRI restriction site in the human Nogo-A sequence and subcloned into Bluescript vector, named Pbsnogoa. To obtain pRK7-hNogo-A, the full length cDNA was inserted into the eukaryotic expression vector pRK-7 by directional cloning.

c) Generation of human NiG (hNiG) expression plasmids (pET28a-hNiG) for bacterial production: A hNiG encoding DNA fragment is subcloned into BamHI/XhoI of pET28a (Novagen), after PCR amplification of the respective coding region from Pbsnogoa, in frame with the N-terminal His- and T7-tag for bacterial expression, using primer sets: forward 5'-GTC GCG GAT CCA TGG AGA CCC TTT TTG CTC TTC-3' (SEQ ID NO: 31); reverse 5'-GTT CTC GAG TTA TGA AGT TTT ACT CAG-3' (SEQ ID NO: 32). The final plasmid is termed pET28a-hNiG. hNiG was then expressed in E. coli BL21 pRP by induction with 1 mM Isopropyl-beta-D-thiogalactopyranoside (IPGT).

d) Generation of mouse NiG-exon3 (mNiG-exon3) expression plasmid: The region encoding mouse exon 3 is amplified from mouse genome BAC template with primers: forward 5'-GTG CGG ATC CAT GGA TTT GAA GGA GCA GC-3' (SEQ ID NO: 33); reverse 5'-GTT TCT CGA GTG AAG TTT TAT TCA GCT C-3' (SEQ ID NO: 34) and subcloned into the BamHI/XhoI cloning sites of pET28a. The final plasmid construct is named pET28a-mNiG-exon3.

Cloning of monkey NiG: PolyA RNA is isolated from frozen monkey brain tissue and cDNA are synthesised using an oligo dT primer. Two overlapping fragments covering the 5' and the 3' region of the cDNA are amplified by PCR using sequence-specific primers and a proofreading enzyme. The primers are designed using the known sequence of the human NiG cDNA. For amplification of the 5' fragment the primers are 5'-TCCACCCCGGCCGCGCCCAA-3' (SEQ ID NO: 35) and 5'-AATGATGGGCAAAGCTGTGCTG-3' (SEQ ID NO: 36), for the 3'-fragment 5'-GGTACAAAGATTGCTTAT-GAAACA-3' (SEQ ID NO: 37) and 5'-AGCAGGGCCAAG-GCAATGTAGG-3' (SEQ ID NO: 38). The two fragments are then subcloned and for each fragment at least 4 independent clones were sequenced. The full length cDNA is assembled by overlapping PCR using the primers mentioned above and the resulting product is cloned and sequenced again.

e) Production of recombinant NogoNiG proteins and the Nogo-A-deletion library as defined above: The bacterial Nogo-A-deletion library is expressed in *Escherichia coli*. Proteins are extracted either by repeated sonication in sonication buffer (20 mM Tris, 50 mM $NaH_2PO_4$, 100 mM NaCl, pH 8.0) with 0.75 mg/ml Lysozyme, by solubilisation with B-Per™ (Pierce) or with 8 M urea. NiG expressed with peIB-leader is obtained from the periplasmic space according to the Novagen protocol for periplasmic protein purification. Supernatants of pET28-constructs are purified using the $Co^{2+}$-Talon™ Metal Affinity Resin (Clontech) in a batch procedure. 8 M urea and B-Per™ solubilised lysates are brought to non-denaturing conditions by increasingly substituting the buffer with sonication buffer during the resin-batch procedure. Proteins are eluted with 250 mM imidazole in sonication buffer on a gravity column (BioRad). NiG proteins are further purified by gel filtration on Superdex 200 HiLoad 16/60. Supernatants of pGEX-6P constructs are purified with G-sepharose column in a batch procedure according to manufacturer indications (Amersham Pharmacia). Cleavage of GST-Nogo-66 is done by incubating solubilised GST-Nogo-66 with PreScission protease and subsequent HPLC purfication. Gel electroelution is performed by preparative SDS-PAGE of IMAC-purified recombinant Nogo and elution with BioRad Electro-Eluter into 50 mM Tris, pH 7.4, 100 mM NaCl, 0.2% (w/v) CHAPS for 1 hr at 250 mA and followed by 30 s of reversed electrode polarities. Protein concentrations of chromatography-purified proteins are determined using Pierce Coomassie Stain and BSA as standard protein. Protein concentrations of gel eluted proteins are estimated based on band intensity of silver-stained gels (Merril C R, Dunau M L, Goldman D (1981) A rapid sensitive silver stain for polypeptides in polyacrylamide gels. Analyt. Biochem. 110:201-207) with BSA as a standard.

f) Production of recombinant NogoA fragments in CHO cells: A 3119 bp fragment resulting from a partial HincII digest of rat Nogo-A cDNA, NiR-G, is cloned into pSecTag2 expression vectors (Invitrogen, Groningen, The Netherlands). Transfection of pNiR-G into CHO cells results in intracellular, cytoplasmic expression of NiR-G. Stable NIR-G CHO cell lines are selected with 250 µg/ml Zeocin (Invitrogen). Recombinant NiR-G from cell lysate is purified over a $Ni^{2+}$-NTA column (Qiagen A G, Basel, Switzerland). Rat NiG-D20 and Nogo-66 are cloned into pAPtag5 vector by PCR. Transfection of pNiG-D20-AP into CHO cells results in NiG-δ20-AP that was secreted into the culture supernatant. Stable pNiG-D20-AP and pNogo-66-AP cell lines were selected with 250 µg/ml Zeocin (Invitrogen). Both cell lines are adapted to serum-free medium (Gibco) conditions and grown in a cell-line chamber (Integra). Supernatants are ten-fold concentrated prior to use, and the concentration of fusion protein is assessed as described elsewhere (Flanagan J G, Leder P (1990) The kit ligand: a cell surface molecule altered in steel mutant fibroblasts. Cell 63:185-194).

g) 3T3 fibroblast and CHO spreading assays: The 3T3 spreading assays are performed as described previously (Spillmann A A, Bandtlow C E, Lottspeich F, Keller F, Schwab M E (1998) Identification and characterization of a bovine neurite growth inhibitor (bNI-220). J. Biol. Chem. 273:19283-19293). CHO spreading assays are performed essentially the same way as for 3T3 fibroblasts. Briefly, CHO cells are split 1:2. 24 hrs later they are trypsinised in PBS-EDTA for 30 s and ~8'000 CHO cells are plated onto culture dishes precoated with 5, 1, 0.5 and 0.2 µg/well NiG or Nogo-66. After 30-45 min the cells are fixed with 4% (w/v) PFA, 5% (w/v) sucrose and then analysed as described Spillmann et al, supra). ~100 cells are counted per well with light microscopy; criterion of spreaded cells: (a) attachement to the dish AND (b) extended morphology indicative for lamellipodia; under light microscopy the cells appear darker and larger than not spreaded, round cells; non-spreaded cells are considered those cells that are (a) not attached to the dish OR (b) attached to the dish, but small, rounded, without detectable lamellipodia protruding on the dish. The ratio between spreaded and not spreaded cells defines the degree of non-permissiveness of the substratum.

h) PC12 Neurite outgrowth assays: PC12 neurite outgrowth assays are performed as described previously (Rubin B P, Spillmann A A, Bandtlow C E, Keller F, Schwab M E (1995) Inhibition of PC-12 cell attachment and neurite outgrowth by detergent solubilized CNS myelin proteins. Europ. J. Neurosci. 7: 2524-2529). PC12 cells (a PC12 cell clone able to grow independently of laminin obtained from Moses Chao, New York) are primed for two days with 50-100 ng/ml NGF (Harlan Bioproducts, Indianapolis) to DMEM, 5% foetal calf serum, 10% horse serum, 100 U/ml Penicillin and 0.5 mg/ml Streptomycin (Pen-Strep from Gibco-BRL). PC12 cells are detachde mechanically, trypsinised for 5 minutes with 0.05% trypsin (Sigma) in HBSS (Gibco) and plated at a density of 3,000-5,000 cells/cm2 in culture medium with 100 ng/ml NGF. Assays were stopped after 24 hrs by adding 4% (w/v) PFA, 5% (w/v) sucrose in PBS, pH8. Cell culture dishes were coated for PC12 cells the same way as for 3T3 cells.

i) Retinal ganglion cell stripe assays: The retinal ganglion cell stripe assay is performed according to Vielmetter (see Vielmetter J, Stolze B, Bonhoeffer F, Stuermer C A (1990) In vitro assay to test differential substrate affinities of growing axons and migratory cells. Exp. Brain Res. 81:283-287) with modifications (see Schmalfeldt M, Bandtlow C E, Dours-Zimmermann M T, Winterhalter K H, Zimmermann D R (2000) Brain derived versican V2 is a potent inhibitor of axonal growth. J. Cell Sci. 113:807-816). Explants are evaluated after fixation with 4% (w/v) PFA, 0.1% (v/v) glutaraldehyde in PBS for 10 min at RT. For immunostainings, fixed explants are blocked for 1 hr at RT with RNO-blocking solution (0.5% (w/v) BSA, 0.3% (w/v) TopBlock (Juro Supply), 0.1% (w/v) $NaN_3$ in PBS), permeabilised for 10 min with 0.05% (v/v) Tx-100 in RNO-blocking solution, frozen for one minute at −20° C. and incubated with primary antibodies (AS Bianca for NiR, AS Laura for Nogo-A, NiR-G, NiG, NiG-D3 and NiG-D20, Novagen mAb anti-T7 for Nogo-C and beta-Gal control protein). After washing with PBS, FITC- and TRITC (FITC: Fluorescein-IsoThioCyanate:

TRITC: Tetramethyl Rhodamine lsoThiocyanate)-conjugated antibodies (Jackson ImmunoResearch Laboratories) are added (1:150) to the explants. The samples are coverslipped in 50% (v/v) glycerol, 25 mM NaHCO$_3$, 40 mM NaCl, 1% (w/v) p-Phenylendiamine (Sigma).

Results:

a) Two regions in the N-terminal part of Nogo-A are inhibitory for spreading of 3T3 fibroblasts: In order to identify the regions of Nogo-A responsible for the inhibition of 3T3 fibroblast spreading, a library of 50 Nogo deletion constructs is made and recombinant proteins are expressed in bacteria (see method 1a). The apparent EC$_{50}$ for inhibition of 3T3 fibroblast spreading was approximately 400-500 ng/0.1 ml Nogo-A coated overnight per cm$^2$ of culture dish (~4 pmol/cm$^2$). Treatment of Nogo-A or its fragments with 8 M urea results in a strong decrease of inhibitory activity, indicating that conformation is important. The analysis of Nogo fragments in the fibroblast spreading assay reveals that at least two stretches of the Nogo-A protein mediate inhibition of the spreading of freshly plated fibroblasts, namely NiR-D2 (aa 59-172) and NiG-D20 (aa 544-725). All the fragments derived from the NiG-region displaying inhibitory activity (e.g. NiG-D4 and NiG-D8) partially overlap with NiG-D20. Minor inhibitory activity at high protein concentration is seen for NiG-D19 within the NiG-D6 region. Nogo-C, Nogo-66 and rat Peptide 4 (shown to be the inhibitory region of Nogo-66 by GrandPréet al., 2000) are not inhibitory for fibroblast spreading. These data show that the anti-spreading activity of Nogo-A on 3T3 fibroblasts resides in two defined stretches located at the N-terminus (NiR-D2) and within the Nogo-A-specific part (NiG-D20) of the protein. Non-specific physico-chemical properties (acidity of the fragments, structural effects due to proline and serine residues) are not responsible for this effect. The C-terminal RTN domain is not involved in the inhibition of fibroblast spreading.

b) NiG-D20 Region of Nogo-A is inhibitory for neurite outgrowth: To determine whether the fragments of Nogo-A that are non-permissive for cell spreading are also inhibitory for neurite outgrowth, a series of bacterially produced Nogo-A fragments as well as eukaryotically produced Nogo-AP chimeras in different neuronal assays are tested. In the stripe assay (method 1), neurites avoid laminin/Nogo-A coated stripes, growing on the laminin-only stripes, whereas stripes coated with laminin/beta-Galactosidase are not circumvented. Full-length Nogo-A is strongly non-permissive for retinal ganglion cell (RGC) neurite outgrowth, while the N-terminal part (NiR) had only marginal effects. Nogo-C activity is indistinguishable from the control protein beta-Galactosidase. The Nogo-A-specific region NiG-D20 appears to contain the main region responsible for the non-permissive activity on RGC neurite outgrowth; the growth cones stop when encountering NiG-D20-coated stripes. The nonpermissive effect is concentration-dependent. At lower Nogo-A concentrations the number of crossing fibers increased. No obvious difference is observed between nasal and temporal RGC neurites concerning their responsiveness to Nogo-A regions. A laminin-independent, NGF-responsive clone of PC12 cells is primed with 50 ng/ml NGF for 24 hrs and then plated onto dishes coated with bacterially produced Nogo fragments at 0.1-3 μg/cm$^2$. Neurite outgrowth is scored one day later. The Nogo-A-specific region (NiG) and its fragment NiG-δ20 strongly inhibited PC12 neurite outgrowth. In contrast, the N-terminal fragment NiR has only minor activity, detectable only at high protein concentration. Nogo-C and Nogo-66 are inactive.

EXAMPLE 2

Presence of Binding Site(s) for NiR-G and NiG-D20 on 3T3 Fibroblasts and Rat Cortical Brain Membranes Methods:

a) Radioactive labelling and binding experiments: IMAC-purified NiG-D20 is iodinated by ANAWA Trading SA (Wangen, Switzerland) (2,030 Ci/mmol) using Lactoperoxidase and purified by reverse-phase HPLC. Membranes from rat brain cortex are prepared as described (Olpe H R, Karlsson G, Pozza M F, Brugger F, Steinmann M, Van Riezen H, Fagg G, Hall R G, Froesti W, Bittiger H (1990) CGP 35348: a centrally active blocker of GABAB receptors. Eur. J. Pharmacol. 187: 27-38). Binding is performed for 1 hr at RT essentially as described (Kaupmann K, Huggel K, Heid J, Flor P J, Bischoff S, Mickel S J, McMaster G, Angst C, Bittiger H, Froestl W, Bettler B (1997) Expression cloning of GABA(B) receptors uncovers similarity to metabotropic glutamate receptors. Nature 386:239-246.) using 1.5 ml tubes preincubated for 2 hrs with 1% (w/v) bovine serum albumin to reduce non-specific binding. Membrane homogenates in HEPES buffer pH 7.4 (125 mM NaCl, 5 mM KCl, 0.6 mM MgCl$_2$, 1.8 mM CaCl$_2$, 20 mM HEPES, 6 mM dextrose) containing protease inhibitors (Rôche Diagnostics, Mannheim, FRG) are incubated with 1.3 nM iodinated NiG-D20 in the absence or presence of increasing concentrations of unlabelled NiG-D20.

b) Flow cytometry: Flow cytometry and cell sorting are performed on a Cytomation MoFlo high-speed cell sorter (Fort Collins, Colo.). The flow cytometer is equipped with an argon-ion/UV Enterprise II laser tuned to 488 nm with 130 mW of power. Fluorescein (FITC) fluorescence is collected through a 530/40 nm bandpass filter. For analysis 3T3 fibroblasts are detached with Cell Dissociation Buffer (Gibco). The pre-formed complex used to detect binding of NiR-G to 3T3 fibroblasts is prepared as follows: NiR-G and anti-Myc antibody (9E10) are incubated at a 1:1 molar ratio for 30 min at 4° C. Next, FITC conjugated F(ab)$_2$ Goat Anti Mouse IgG is added and incubated for additional 30 min at 4° C. The resulting molar ratio of the trimeric complex is 1:1:0.5. The complex is added to 1×10$^6$ 3T3 fibroblasts in a final volume of 0.1 ml, incubated for 2 hrs at 4° C., washed, and analysed by flow cytometry.

Results:

Presence of binding site(s) for Nogo-A-specific active fragments on 3T3 fibroblasts and rat cortical brain membranes: Since the NiR-D2 and NiG-D20 regions of Nogo-A are inhibitory for cell spreading and neurite outgrowth despite the absence of Nogo-66 and independently of NgR, the presence of a separate, Nogo-A-specific receptor has to be postulated. Thus binding studies are performed of multimerised, myc-tagged and IMAC-purified NIR-G to living 3T3 fibroblasts that are analysed by flow cytometry. Ab-complexed NiR-G is binding efficiently to 3T3 cells as seen by a fluorescence shift of over 90% of the 3T3 cells. In contrast, 3T3 cells are not labelled after incubation with the 9E10 primary mouse anti-myc mAb complexed with a FITC-conjugated secondary F(ab)$_2$ goat anti-mouse IgG nor with the secondary Ab alone. To test binding of NiG-D20 to rat cortical membranes, [$^{125}$I]-labelled NiG-D20 in a radioligand binding assay is used. At a concentration of 1.3 nM of [$^{125}$I]-NiG-D20, evidence for a specific NiG-D20 binding sites on brain membranes as shown by a concentration-dependent competition of radioligand binding by unlabelled NiG-D20 is found. These results show that aminoterminal fragments of Nogo-A can bind to the surface of 3T3 cells and to rat cortical membranes, demonstrating the presence of membrane-bound, Nogo-A-specific binding sites or receptor(s).

EXAMPLE 3

Generation of Mouse 11C7-IgG1

Mice (C3H- and C57BI6/J-strains) are immunised subcutaneously with the synthetic peptide SYDSIKLEPENPPPY-EEA (=rat NogoA__623-640; SEQ ID NO: 1), corresponding to a particular epitope in NiG-D20. This epitope is highly conserved in human, cynomologus monkey and mouse NiG-D20 Nogo-A specific region and starts at amino acid 623 and ends at amino acid 640 of the human NogoA amino acid sequence (SEQ ID NO: 5) (See also sequence alignment: FIG. 1).

mAb 11C7 has been obtained out of a fusion of rat NogoA__623-640 with the carrier protein Key hole limped hemagglutinin (KLH) immunised mice. Monoclonal antibodies have been screened by ELISA on rat NogoA__623-640-KLH, rat NogoA__623-640 free peptide and a nonrelated peptide-KLH. In a further screen, the mAbs have been tested by ELISA on NiR-G versus b-Galactosidase, both expressed as his-tagged proteins and purified by metal affinity chromatography. Subsequently, the mAbs have been tested for recognition of Nogo-A on Western blot of oligodendrocyte and brain lysates (rat origin). Antibodies are tested for recognition of the protein in immunocytochemistry of rat Nogo-A-transfected CHO or COS cells and of endogenous Nogo-A of rat oligodendrocytes (permeabilised cells). They have also been tested for surface binding to living rat oligodednrocytes. Species crossreactivity is tested on recombinant NiG of rat, mouse, human and bovine origin by ELISA and on endogenous rat, mouse, human and monkey Nogo-A by Western blot of tissue or cell extracts.

Western blot analysis: SDS-PAGE and Westernblotting are performed as described earlier (Huber A B, Weinmann O, Brosamle C, Oertle T, Schwab M E (2002) Patterns of Nogo mRNA and protein expression in the developing and adult rat and after CNS lesions. J. Neurosci. 22: 3553-3567), blocking is done with 3% (w/v) Top Block (Juro Supply, Lucerne, Switzerland). Antibodies are diluted as follows: Purified monoclonal 11C7 or hybridoma supernatants 1:150. Secondary antibodies are HRP-conjugate anti-mouse ((Pierce; 1:5000,) 1:50,000). Hybridisation with the 11C7 antibody is carried out over night at 4° C. For detection the ECL detection reagents from Amersham Pharmacia are used.

Results:

The 11C7 mAb identifies the 190 kD Nogo-A band on a Western blot of oligodendrocyte cell culture homogenate. 11C7 also identifies human NiG, Cynomolgus NiG cell lysate and rat NiG-D20 in western blots. 11C7 mAb is characterised as a IgG1 isotype (IsoStrip Kit, Roche).

EXAMPLE 4

Characterisation of the Mouse 11C7 mAb

Immunocytochemistry: Optic nerve oligodendrocytes are prepared as described (Schwab, Caroni, 1988, Neuron). Three to five day-old cultures grown on poly-L-lysine coated coverslips are washed twice with PBS, fixed in 4% (w/v) paraformaldehyde (PFA), 5% (w/v) sucrose in PBS for 15 min at room temperature (RT) and non-specific binding is blocked with 10% (v/v) FCS. Cells were then incubated with mouse 11C7 (1:100). Secondary antibodies are goat-anti-mouse TRITC (Jackson ImmunoResearch Laboratories). For cell surface staining, two day-old rat optic nerve cultures are incubated with monoclonal antibody in medium for 25 min at RT. Secondary alkaline phosphatase conjugated antibodies (Milan Analytica, Lausanne) are used at 1:7,500 in 0.1 M maleic acid with 1% (w/v) blocking reagent (1 hr). The cultures are washed twice with maleic acid buffer, once with alkaline phosphatase buffer (0.1 M Tris-HCl pH 9.5, 0.1 M NaCl, 5 mM MgCl$_2$) and the staining is developed for 3 hrs at room temperature with 0.175 mg/ml BCIP (Sigma) and 0.338 mg/ml NBT (Sigma) in alkaline phosphatase buffer.

NogoA__623-640 epitope of Nogo-A present at the cell surface of cultured oligodendrocytes: Living cultures of oligodendrocytes incubated with mouse 11C7 mAb stain the differentiated oligodendrocyte cell bodies and their radial processes. The control mouse IgG and the antibodies against the intracellular protein CNPase do not stain the living cells. Preincubation of mouse 11C7 with the corresponding immunogenic peptide (=rat NogoA__623-640 SED ID NO: 1) reduces staining to background levels (competitive assay). Cell surface staining is present on all major and small processes and on the cell body. Thus, the Nogo-A specific part of the molecule recognised by mouse 11C7 mAb is exposed to the extracellular space on the plasma membrane of oligodendrocytes.

Production and Purification of mouse 11C7 mAb:_A 10-L glas bioreactor is used for continuous-mode cultivation of the hybridoma clone producing the mouse 11C7 mAb. The bioreactor is equipped with a marine impeller placed in a center tube for gentle agitation, a spin filter for cell retention, and coiled silicone tubing for bubble-free aeration. The hybridoma cells are cultivated in our RPMI based serum free medium. The medium is inoculated with cells at $3.7 \times 10^5$/ml. After 28 hours continuous medium flow through the bioreactor is started with a rate of 0.5 fermentor volumes/day (5 liters/day). Another 24 hours later the flow rate is increased to its final level of 1 fermentor volume/day (10 liters/day). After 1 week the culture reaches a steady state with $11 \times 10^5$ cells/ml and the process is continued for another week. The titer of the mouse 11C7 mAb is determined daily by HPLC. A total of 150 liters culture supernatant is harvested from the bioreactor, sterile filtered for removal of cells and cell debris. 150 L culture supernatant are concentrated to about 6 L using a Pellikon tangential flow device (Millipore; 10 kDa cut-off). The concentrated supernatant is purified in 3 runs over a 220 ml bed volume column of Protein A Sepharose CI-4B (Pharmacia; 11 cm bed height). Briefly, the culture supernatant after pH correction to 8.1 is loaded at 4 ml/min and the column washed to baseline at 8 ml/min using 100 mM Na$_2$HPO$_4$, pH 8.1. Bound material is finally eluted at 8 ml/min using 50 mM NaH$_2$PO$_4$, pH 3.0, 140 mM NaCl and immediately neutralized (pH 7.0) with 5 N NaOH and sterile filtered. Absorbance is monitored at 280 nm. Portion of the purified material are eventually further concentrated by ultrafiltration and/or dialyzed against PBS. All the buffers used in the purification are filtered on a 10 kDa ULTRASETTE™ tangential flow device (Filtron Technology Corporation) in order to remove possible endotoxin contaminations. For the same reason the Protein A resin is extensively washed with 20% ethanol and all tubings/pumps treated with 0.1 M NaOH prior to use. Protein concentration is measured spectrophotometrically at 280 nm using a reference absorption of 1.35 for 1 mg/ml. Purity is routinely assessed by SDS-PAGE under reducing conditions using 4-20% Novex gradient gels. Endotoxin content is measured by the classical Limulus Amoebocyte Lysate (LAL) reaction according to the manufacturer instructions (Endotell A G, Allschwil, Switzerland).

Generation of $F_{ab}$ fragments: A portion of mouse 11C7 mAb is extensively dialyzed against 100 mM Na-acetate, pH 5.5, 2 mM EDTA and adjusted to a concentration of 6 mg/ml. $F_{ab}$ fragments are generated by papain digestion (1:200 w/w ratio) in the presence of 0.25 mM cysteine. The reaction is allowed to proceed for 16 hours at 37° C. and then stopped by the addition of the specific papain inhibitor E64 (N-[N-(L-3-trans-carboxirane-2-carbonyl)-L-leucyl]-agmatine) in large excess (10 µM). The digested antibody is then passed over a column of protein A Sepharose Fast Flow in order to remove intact material and Fc fragments. The $F_{ab}$ fraction is extensively dialysed against PBS and concentrated to about 3 mg/ml. (Papain and E64 are from Roche Molecular Biochemicals).

HPLC, Mass Spectrometry and N-terminal amino acid sequencing of $V_L$ and $V_H$ regions:

a) Reduction and Alkylation: Purified, dried 11C7 antibody are dissolved in 40 µl of 8M urea, 0.4M $NH_4HCO_3$, pH 8.3. 60 ug DTT (Calbiochem), pre-dissolved in 10 ul of the same buffer as the protein, are added. Reduction is performed at 50° C. for 30 min under argon (100 fold molar excess of DTT over protein thiols). After reduction, the sample is cooled to room temperature. 304 ug of Iodoacetamide (Sigma Ultra, I-1149) dissolved in the same buffer as the protein is added. Carboxamidomethylation is carried out at room temperature for 15 min in the dark. 1 µl β-mercaptoethanol is added to quench the reaction.

b) Isolation of Heavy- and Light-Chain: Carboxamidomethylated heavy and light chains of antibody are isolated by Reverse Phase High Pressure Liquid Chromatography (RP-HPLC) on a Hewlett Packard 1090M HPLC System with DR5 pumping system and diode-array UV detector. The conditions for chromatography are: PerSeptive Biosystems Poros 2.1×100 mm column packed with R1/H material; flow is 0.5 ml/min; solvents: (A) 0.1% TFA in water and (B) 0.09% TFA/acetonitril/water 9:1; gradient 25-70% B in 8 minutes at 80° C.; detection at 218/280 nm.

c) LC-ESI-MS: Mass spectrometry is carried out using a Q-Tof (Micromass, Manchester, UK) quadrupole time-of-flight hybrid tandem mass spectrometer equipped with a Micromass Z-type electrospray ionization source (ESI). Acquisition mass range is typically m/z 500-2000. Data are recorded and processed using MassLynx software. Calibration of the 500-2500 m/z scale is achieved by using the multiple-charged ion peaks of horse heart myoglobin (MW 16951.5).

d) HPLC-MS of heavy and light chain: Separation of reduced and carboxamidomethylated heavy and light chain is performed on a HP1100 HPLC system (Hewlett Packard, Palo-Alto, Calif., USA) employing a 1 mm×150 mm LC Packings column packed with Perseptive Biosystems POROS R1/H. The column is held at 60° C. Sample volumes of 10 µl are injected onto the column using a CTC PAL autosampler (CTC, Zwingen, Switzerland) fitted with a Valco model C6UW HPLC valve (Valco, Houston, Tex., USA) and a 10 µl injection loop. HPLC was controlled by MassLynx software (Micromass, Manchester, UK). UV detection is at 214 nm. Eluent A is water containing 0.05% TFA. Eluent B is a 1:9 mixture of water:acetonitrile containing 0.045% TFA. A gradient from 20% B to 90% B is run in 20 minutes at 80° C. The flow rate is typically 60 µl/min. The total flow from the LC system is introduced into the UV detection cell, then the ESI source without any splitting. The HPLC system is controlled and the signal from the UV detector is processed using MassLynx software (Micromass, Manchester, UK). The following 5 signals are detected:

TABLE 1

| Measured: | Signal interpretation |
|---|---|
| A = 50959.0 Da | H-Chain with carboxamidomethyl-cysteine (CAMCys)* |
| B = 51119.5 Da | Signal A + 162 Da (=hexose)** |
| C = 51086.0 Da | Signal A + 127 (Lys), H-Chain with CAMCys* |
| D = 51251.0 Da | Signal C + 162 Da (=hexose)** |
| E = 24464.8 Da | L-Chain with CAMCys |

*There are two types of H-chain present, one with and one without Lys at the C-terminal end. The ratio of both forms is approximately 50:50%.
**Both types of H-chains have two corresponding glycosylated forms (+162)

d) N-terminal amino acid sequencing of $V_L$ and $V_H$ regions: Collected H+L chains peaks form HPLC are used for sequence analysis. Amino acid sequences are determined on a Hewlett Packard G1000A N-terminal Protein Sequencing System. The system performs automated Edman chemistry on protein samples retained on miniature adsorptive biphasic columns. An optimized chemistry method (double couple 3.0) is used to enhance chemical efficiency, minimize lags and herewith extend sequence analysis to about 50 residues. Analysis of PTH-amino acids is performed on an on-line Hewlett Packard HP1090 HPLC System equipped with a ternary pumping system and a narrowbore (2.1 mm×25 cm).PTH column.

Results:

From mass analysis homogeneous heavy and light chain of mouse 11C7-IgG1 are determined. The H-chain is single glycosylated and there are two forms with a difference on the C-terminal Lysine. Total mass analysis of heavy and light chain shows a single mass for both chains. HPLC chromatography of mouse 11C7-IgG1 shows a single peak. After HPLC purification followed by reduction and alkylation pure heavy and light chain are available. N-terminal sequence degradation is performed on light-chain and heavy-chain. 45 to 55 amino acids from the N-terminal sequence of L-chain and H-chain are identified by sequence degradation.

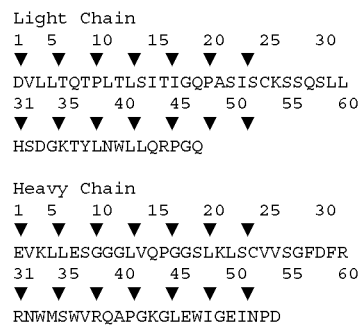

EXAMPLE 5

Cloning of the Heavy and Light Chain Genes of Mouse 11C7 mAb

Total RNA is prepared from $10^7$ hybridoma cells (clone 11C7) using TriPure reagent (Roche diagnostics, Germany, Cat.# 1667157) according to the manufacturers instructions. For cDNA synthesis, mRNA is isolated from above prepared total RNA using Oligotex Resin (Qiagen, Germany, cat. # 70022).

cDNA is generated by reverse transcription using the following conditions: 2 µl mRNA, 2 µl 10× reverse transcription buffer, 2 µl (dT)$_{20}$ primer (10 µM), 0.5 µl RNasin (Promega, 40 U/ml), 2 µl dNTPs (5 mM each), 1 µl Omniscript™ reverse transcriptase (Qiagen, Cat # 205110), 10.5 µl ddH$_2$O, Reaction: 1 hr at 37° C. For PCR amplification of cDNA encoding for the V$_H$ and V$_L$ the proofreading enzyme ProofStart™ DNA polymerase is used.

PCR of light and heavy chain: Reaction mix: 2 µl cDNA, 5 µl 10× reaction buffer, 3 µl dNTPs (5 mM each), 2 µl, 5'primer (10 µM) (see Table 2), 2 µl 3'primer (10 µM) (see Table 2), 1 µl ProofStart (Qiagen, Cat # 202203), 36 µl ddH$_2$O. PCR conditions: 95° C./5 min, (95° C./40 sec, 53° C./1 min, 72° C. 1 min)×35, 72° C./10 min. The resulting PCR products are ligated directly into pCRbluntTOPO (Invitrogen). The ligation mix is transfected into TOP 10 cells (Invitrogen) and several clones are picked. The nucleotide sequences of the variable part of the heavy chain of the 11C7 mAb (V-H, SEQ ID NO: 43) and of the light chain of the 11C7 mAb (V-L, SEQ ID NO: 44) cDNas are determined on an ABI sequencer. The subsequent amino acid sequence of V-H and V-L are shown in SEQ ID NO: 2 (V-H) and SEQ ID NO: 3 (V-L). Primers used for PCR amplification of the V$_H$ and V$_L$ cDNAs; all primers are synthesized by MWG Biotech, Germany.

TABLE 2

| Primer | Sequence | SEQ ID NO: |
|---|---|---|
| 5'-V$_L$ leader | AATATGAGTCCTGCCCAGTTCCTGTTTC | 39 |
| 3'Cκ | TTAGGAATTCCTAACACTCTCCCCTGTTGAAG | 40 |
| 5'-V$_H$ leader | AATATGGATTTTGGGCTGATTTTTTTTATTG | 41 |
| 3'-C$_H$ hinge | AATTGGGCAACGTTGCAGGTGACG | 42 |

EXAMPLE 6

Binding of 11C7 and Fab to Nogo-A Domains Using ELISA

Greiner 96 well PS plates (#655161) are coated with 0.4-2 ug/ml Nogo protein fragments in PBS (100ul/well) covered and incubated 4 hours at room temperature. Plates are flicked and refilled with 200 ul/well blocking buffer (PBS+2% BSA), covered and incubated. 1 h at RT or overnight at 4° C., then washed 4 times with water and PBS. Different concentrations of mouse 11C7 mAb or 11C7 Fab are diluted in PBS+2% BSA (100 u/well), and incubated 2 h at RT or overnight at 4° C. Wash step is repeated and Goat anti-mouse IgG conjugated with horse radish peroxidase (HRP) at a dilution of 1:5000 (ICN #55550) in PBS/0.1% BSA/0.1% Nonidet 40 (100 uVwell) is added and incubated. 2h at RT or overnight at 4° C. and wash step is repeated. HRP reaction is started by adding 100 uvwell BM blue POD (Roche #1484281) and incubafed in the dark at RT for 15 minutes. H2SO4 50 ul/well 1 M is added to stop HRP substrate reaction and the optical density is determinated using a microplate reader (Packard Spectra Count) set to 450 nm.

The mouse 11C7 mAb binds to human NiG, rat NiG, mouse NiG, rat NiG-D20 and peptide 472 at very low concentrations of 0.02 to 2.5 nM. Binding to human NiG, rat NiG, mouse NiG at very low concentration is confirmed by the very high affinity (Kd 0.1-0.44 nM Biosensor affinity measurements) and is consistent with the fact that 472 peptide with the exception of 2-3 amino acids is identical in human compared to rat and mouse equivalent region. The specificity of the binding is indicated by the fact that the mouse 11C7 mAb does not show any binding at all to rat NiG-D6 and Nogo-66 fragments over the same concentration range. The Fab monovalent fragment bound to human NiG and rat NiG-D20 at concentrations 0.025 to 25 nM and showed no binding to rat NiG-D6 and Nogo-66 fragments over the same concentration range. The Kd measured by Biosensor was 7.14 nM for human NiG.

EXAMPLE 7

Biosensor Affinity Measurements for Mouse 11C7-IgG1 and Fab to Nogo-A Domains

The affinity of the mouse 11C7 mAb and of the 11C7 Fab are measured by surface plasmon resonance (SPR) using a BIAcore 2000 optical biosensor (Biacore, Uppsala, Sweden) according to the manufacture's instructions (see FIG. 2). Recombinant human, mouse, and rat NIG are covalently attached to three separate flow cells of a CM5 sensor chip using amine-coupling chemistry. Briefly; the carboxymethlyladed dextran matrix is activated by injecting 35 ul of a solution containing 0.025M NHS and 0.1M EDC. For the immobilization on the sensor chip the recombinant mouse, human, and rat NIG are diluted in 0.01M citrate buffer at a pH varying between 3.5 and 4.5 and injected at a flow rate of 5 ul/min to achieve coupling levels allowing affinity measurements. The deactivation of the remaining NHS-ester group is performed by injection of 35 ul of 1M ethanolamine hydrochloride (pH 8.5). The surface of the sensor chip is regenerated by injecting 5 ul 0.1M HCl. For the measurement of the affinity the antibodies are injected at different concentration, ranging from 0.50 nM to 100 nM at a flow rate of 200 ul/min. After each injection the sensor chip surface is regenerated with the injection of 10 ul 0.1M HCl without loss of binding activity on the surface. The kinetic constants, ka and kd and the affinity constants KA and KD are evaluated using the BIAevaluations 3.0 software supplied by the manufacturer.

Affinity measurement in BIAcore: The kinietc and the affinity binding constants of the mouse 11C7 mAb and the 11C7 derived monovalent Fab fragment to recombinat NogoA are measured in real time using surface plasmon resonance (SPR) technology (Biacore). For this analysis recombinant human, mouse and rat NIGs are coupled on three independent sensor chip surfaces and different concentrations of the antibodies are injected. Kinetic parameters of the binding interactions are derived from the sensorgrams by non-linear curve fitting. The affinity constants at equilibrium of mouse 11C7-IgG1 are KD=0.1 nM, KD=0.4 nM and KD=0.19 nM for human, rat, and mouse NIG respectively (table 3). For the 11C7 derived Fab fragment the affinity constant to human NIG is KD=7.14 nM. The lower affinity of the Fab fragment results from a decrease of both kinetic constants, association and dissociation (ka, kd). Lower affinity of the Fab fragment compared to the complete antibody is probably related to the avidity effect, which is lacking in the monomeric Fab.

TABLE 3

| | Ka (1/Ms) | kd (1/s) | KA (M$^{-1}$) | KD (M) |
|---|---|---|---|---|
| 11C7 | | | | |
| HumanNIG | $4.48 \times 10^5$ | $4.6 \times 10^{-5}$ | $9.73 \times 10^9$ | $1.03 \times 10^{-10}$ |
| Rat NIG | $8.76 \times 10^5$ | $3.89 \times 10^{-4}$ | $2.25 \times 10^9$ | $4.44 \times 10^{-10}$ |
| Mouse NIG | $5.52 \times 10^5$ | $1.06 \times 10^{-4}$ | $5.2 \times 10^9$ | $1.92 \times 10^{-10}$ |

TABLE 3-continued

| | Ka (1/Ms) | kd (1/s) | KA (M$^{-1}$) | KD (M) |
|---|---|---|---|---|
| 11C7 Fab | | | | |
| HumanNIG | $7.29 \times 10^4$ | $5.28 \times 10^{-4}$ | $1.4 \times 10^8$ | $7.14 \times 10^{-9}$ |

The invention claimed is:

1. An isolated human Nogo_A623-640 binding molecule which comprises a heavy chain variable domain or fragment thereof, and wherein said heavy chain variable domain or fragment thereof comprises in sequential order SEQ ID NO:8, SEQ ID NO:9 and SEQ ID NO:10; and a light chain variable domain or fragment thereof, and wherein said light chain variable domain or fragment thereof comprises in sequential order SEQ ID NO:11, SEQ ID NO:12 and SEQ ID NO:13.

2. A composition comprising the binding molecule according to claim 1, and a pharmaceutically acceptable carrier.

3. A composition comprising the binding molecule according to claim 1, and at least one carrier or diluent.

* * * * *

```
                        SEQUENCE LISTING

<160> NUMBER OF SEQ ID NOS: 48

<210> SEQ ID NO 1
<211> LENGTH: 18
<212> TYPE: PRT
<213> ORGANISM: Rattus norvegicus
<220> FEATURE:
<221> NAME/KEY: PEPTIDE
<222> LOCATION: (1)..(18)
<223> OTHER INFORMATION: rat NogoA_623-640

<400> SEQUENCE: 1

Ser Tyr Asp Ser Ile Lys Leu Glu Pro Glu Asn Pro Pro Tyr Glu
1               5                  10                  15

Glu Ala

<210> SEQ ID NO 2
<211> LENGTH: 221
<212> TYPE: PRT
<213> ORGANISM: Mus musculus
<220> FEATURE:
<221> NAME/KEY: CHAIN
<222> LOCATION: (1)..(221)
<223> OTHER INFORMATION: Variable part of Heavy Chain of 11C7 with
      leader sequence

<400> SEQUENCE: 2

Met Asp Phe Gly Leu Ile Phe Phe Ile Val Gly Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Val Val Ser Gly Phe Asp Phe Arg
        35                  40                  45

Arg Asn Trp Met Ser Trp Val Arg Gln Ala Pro Gly Lys Gly Leu Glu
    50                  55                  60

Trp Ile Gly Glu Ile Asn Pro Asp Ser Ser Lys Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Val Ser Thr Val Arg Ser Glu Asp Thr Ala Leu Tyr
            100                 105                 110

Tyr Cys Val Arg Pro Val Trp Met Tyr Ala Met Asp Tyr Trp Gly Gln
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175
```

```
Trp Asn Ser Gly Ser Leu Ser Ser Gly Val His Thr Phe Pro Ala Val
            180                 185                 190

Leu Gln Ser Asp Leu Tyr Thr Leu Ser Ser Val Thr Val Pro Ser
        195                 200                 205

Ser Thr Trp Pro Ser Glu Thr Val Thr Cys Asn Val Ala
    210                 215                 220

<210> SEQ ID NO 3
<211> LENGTH: 238
<212> TYPE: PRT
<213> ORGANISM: Mus musculus
<220> FEATURE:
<221> NAME/KEY: CHAIN
<222> LOCATION: (1)..(238)
<223> OTHER INFORMATION: Light Chain of 11C7 with leader sequence

<400> SEQUENCE: 3

Met Ser Pro Ala Gln Phe Leu Phe Leu Leu Val Leu Trp Ile Arg Glu
1               5                   10                  15

Thr Ser Gly Asp Val Leu Leu Thr Gln Thr Pro Leu Thr Leu Ser Ile
            20                  25                  30

Thr Ile Gly Gln Pro Ala Ser Ile Ser Cys Lys Ser Ser Gln Ser Leu
        35                  40                  45

Leu His Ser Asp Gly Lys Thr Tyr Leu Asn Trp Leu Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Leu Tyr Tyr Cys
            100                 105                 110

Trp Gln Gly Thr His Phe Pro Gln Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Gly Glu Cys
225                 230                 235

<210> SEQ ID NO 4
<211> LENGTH: 3919
<212> TYPE: DNA
<213> ORGANISM: Homo sapiens
<220> FEATURE:
<221> NAME/KEY: CDS
<222> LOCATION: (1)..(3579)
<223> OTHER INFORMATION: Human NogoA

<400> SEQUENCE: 4
```

-continued

| | |
|---|---|
| atg gaa gac ctg gac cag tct cct ctg gtc tcg tcc tcg gac agc cca<br>Met Glu Asp Leu Asp Gln Ser Pro Leu Val Ser Ser Ser Asp Ser Pro<br>1               5                   10                  15 | 48 |
| ccc cgg ccg cag ccc gcg ttc aag tac cag ttc gtg agg gag ccc gag<br>Pro Arg Pro Gln Pro Ala Phe Lys Tyr Gln Phe Val Arg Glu Pro Glu<br>                20                  25                  30 | 96 |
| gac gag gag gaa gaa gag gag gag gag gag gac gag gac gaa gac<br>Asp Glu Glu Glu Glu Glu Glu Glu Glu Glu Asp Glu Asp Glu Asp<br>            35                  40                  45 | 144 |
| ctg gag gag ctg gag gtg ctg gag agg aag ccc gcc gcc ggg ctg tcc<br>Leu Glu Glu Leu Glu Val Leu Glu Arg Lys Pro Ala Ala Gly Leu Ser<br>50                  55                  60 | 192 |
| gcg gcc cca gtg ccc acc gcc cct gcc gcc ggc gcg ccc ctg atg gac<br>Ala Ala Pro Val Pro Thr Ala Pro Ala Ala Gly Ala Pro Leu Met Asp<br>65                  70                  75                  80 | 240 |
| ttc gga aat gac ttc gtg ccg ccg gcg ccc cgg gga ccc ctg ccg gcc<br>Phe Gly Asn Asp Phe Val Pro Pro Ala Pro Arg Gly Pro Leu Pro Ala<br>                85                  90                  95 | 288 |
| gct ccc ccc gtc gcc ccg gag cgg cag ccg tct tgg gac ccg agc ccg<br>Ala Pro Pro Val Ala Pro Glu Arg Gln Pro Ser Trp Asp Pro Ser Pro<br>                100                 105                 110 | 336 |
| gtg tcg tcg acc gtg ccc gcg cca tcc ccg ctg tct gct gcc gca gtc<br>Val Ser Ser Thr Val Pro Ala Pro Ser Pro Leu Ser Ala Ala Ala Val<br>            115                 120                 125 | 384 |
| tcg ccc tcc aag ctc cct gag gac gac gag cct ccg gcc cgg cct ccc<br>Ser Pro Ser Lys Leu Pro Glu Asp Asp Glu Pro Pro Ala Arg Pro Pro<br>130                 135                 140 | 432 |
| cct cct ccc ccg gcc agc gtg agc ccc cag gca gag ccc gtg tgg acc<br>Pro Pro Pro Pro Ala Ser Val Ser Pro Gln Ala Glu Pro Val Trp Thr<br>145                 150                 155                 160 | 480 |
| ccg cca gcc ccg gct ccc gcg gcg ccc ccc tcc acc ccg gcc gcg ccc<br>Pro Pro Ala Pro Ala Pro Ala Ala Pro Pro Ser Thr Pro Ala Ala Pro<br>                165                 170                 175 | 528 |
| aag cgc agg ggc tcc tcg ggc tca gtg gat gag acc ctt ttt gct ctt<br>Lys Arg Arg Gly Ser Ser Gly Ser Val Asp Glu Thr Leu Phe Ala Leu<br>                180                 185                 190 | 576 |
| cct gct gca tct gag cct gtg ata cgc tcc tct gca gaa aat atg gac<br>Pro Ala Ala Ser Glu Pro Val Ile Arg Ser Ser Ala Glu Asn Met Asp<br>            195                 200                 205 | 624 |
| ttg aag gag cag cca ggt aac act att tcg gct ggt caa gag gat ttc<br>Leu Lys Glu Gln Pro Gly Asn Thr Ile Ser Ala Gly Gln Glu Asp Phe<br>210                 215                 220 | 672 |
| cca tct gtc ctg ctt gaa act gct gct tct ctt cct tct ctg tct cct<br>Pro Ser Val Leu Leu Glu Thr Ala Ala Ser Leu Pro Ser Leu Ser Pro<br>225                 230                 235                 240 | 720 |
| ctc tca gcc gct tct ttc aaa gaa cat gaa tac ctt ggt aat ttg tca<br>Leu Ser Ala Ala Ser Phe Lys Glu His Glu Tyr Leu Gly Asn Leu Ser<br>                245                 250                 255 | 768 |
| aca gta tta ccc act gaa gga aca ctt caa gaa aat gtc agt gaa gct<br>Thr Val Leu Pro Thr Glu Gly Thr Leu Gln Glu Asn Val Ser Glu Ala<br>                260                 265                 270 | 816 |
| tct aaa gag gtc tca gag aag gca aaa act cta ctc ata gat aga gat<br>Ser Lys Glu Val Ser Glu Lys Ala Lys Thr Leu Leu Ile Asp Arg Asp<br>            275                 280                 285 | 864 |
| tta aca gag ttt tca gaa tta gaa tac tca gaa atg gga tca tcg ttc<br>Leu Thr Glu Phe Ser Glu Leu Glu Tyr Ser Glu Met Gly Ser Ser Phe<br>290                 295                 300 | 912 |
| agt gtc tct cca aaa gca gaa tct gcc gta ata gta gca aat cct agg<br>Ser Val Ser Pro Lys Ala Glu Ser Ala Val Ile Val Ala Asn Pro Arg<br>305                 310                 315                 320 | 960 |

```
gaa gaa ata atc gtg aaa aat aaa gat gaa gaa gag aag tta gtt agt    1008
Glu Glu Ile Ile Val Lys Asn Lys Asp Glu Glu Lys Leu Val Ser
                325                 330                 335 aat aac atc ctt cat aat caa caa gag tta cct aca gct ctt act aaa    1056
Asn Asn Ile Leu His Asn Gln Gln Glu Leu Pro Thr Ala Leu Thr Lys
                340                 345                 350 ttg gtt aaa gag gat gaa gtt gtg tct tca gaa aaa gca aaa gac agt    1104
Leu Val Lys Glu Asp Glu Val Val Ser Ser Glu Lys Ala Lys Asp Ser
                355                 360                 365 ttt aat gaa aag aga gtt gca gtg gaa gct cct atg agg gag gaa tat    1152
Phe Asn Glu Lys Arg Val Ala Val Glu Ala Pro Met Arg Glu Glu Tyr
370                 375                 380 gca gac ttc aaa cca ttt gag cga gta tgg gaa gtg aaa gat agt aag    1200
Ala Asp Phe Lys Pro Phe Glu Arg Val Trp Glu Val Lys Asp Ser Lys
385                 390                 395                 400 gaa gat agt gat atg ttg gct gct gga ggt aaa atc gag agc aac ttg    1248
Glu Asp Ser Asp Met Leu Ala Ala Gly Gly Lys Ile Glu Ser Asn Leu
                405                 410                 415 gaa agt aaa gtg gat aaa aaa tgt ttt gca gat agc ctt gag caa act    1296
Glu Ser Lys Val Asp Lys Lys Cys Phe Ala Asp Ser Leu Glu Gln Thr
                420                 425                 430 aat cac gaa aaa gat agt gag agt agt aat gat gat act tct ttc ccc    1344
Asn His Glu Lys Asp Ser Glu Ser Ser Asn Asp Asp Thr Ser Phe Pro
                435                 440                 445 agt acg cca gaa ggt ata aag gat cgt tca gga gca tat atc aca tgt    1392
Ser Thr Pro Glu Gly Ile Lys Asp Arg Ser Gly Ala Tyr Ile Thr Cys
450                 455                 460 gct ccc ttt aac cca gca gca act gag agc att gca aca aac att ttt    1440
Ala Pro Phe Asn Pro Ala Ala Thr Glu Ser Ile Ala Thr Asn Ile Phe
465                 470                 475                 480 cct ttg tta gga gat cct act tca gaa aat aag acc gat gaa aaa aaa    1488
Pro Leu Leu Gly Asp Pro Thr Ser Glu Asn Lys Thr Asp Glu Lys Lys
                485                 490                 495 ata gaa gaa aag aag gcc caa ata gta aca gag aag aat act agc acc    1536
Ile Glu Glu Lys Lys Ala Gln Ile Val Thr Glu Lys Asn Thr Ser Thr
                500                 505                 510 aaa aca tca aac cct ttt ctt gta gca gca cag gat tct gag aca gat    1584
Lys Thr Ser Asn Pro Phe Leu Val Ala Ala Gln Asp Ser Glu Thr Asp
                515                 520                 525 tat gtc aca aca gat aat tta aca aag gtg act gag gaa gtc gtg gca    1632
Tyr Val Thr Thr Asp Asn Leu Thr Lys Val Thr Glu Glu Val Val Ala
530                 535                 540 aac atg cct gaa ggc ctg act cca gat tta gta cag gaa gca tgt gaa    1680
Asn Met Pro Glu Gly Leu Thr Pro Asp Leu Val Gln Glu Ala Cys Glu
545                 550                 555                 560 agt gaa ttg aat gaa gtt act ggt aca aag att gct tat gaa aca aaa    1728
Ser Glu Leu Asn Glu Val Thr Gly Thr Lys Ile Ala Tyr Glu Thr Lys
                565                 570                 575 atg gac ttg gtt caa aca tca gaa gtt atg caa gag tca ctc tat cct    1776
Met Asp Leu Val Gln Thr Ser Glu Val Met Gln Glu Ser Leu Tyr Pro
                580                 585                 590 gca gca cag ctt tgc cca tca ttt gaa gag tca gaa gct act cct tca    1824
Ala Ala Gln Leu Cys Pro Ser Phe Glu Glu Ser Glu Ala Thr Pro Ser
                595                 600                 605 cca gtt ttg cct gac att gtt atg gaa gca cca ttg aat tct gca gtt    1872
Pro Val Leu Pro Asp Ile Val Met Glu Ala Pro Leu Asn Ser Ala Val
                610                 615                 620 cct agt gct ggt gct tcc gtg ata cag ccc agc tca tca cca tta gaa    1920
Pro Ser Ala Gly Ala Ser Val Ile Gln Pro Ser Ser Ser Pro Leu Glu
```

-continued

```
            625                 630                 635                 640 gct tct tca gtt aat tat gaa agc ata aaa cat gag cct gaa aac ccc         1968
Ala Ser Ser Val Asn Tyr Glu Ser Ile Lys His Glu Pro Glu Asn Pro
                645                 650                 655 cca cca tat gaa gag gcc atg agt gta tca cta aaa aaa gta tca gga         2016
Pro Pro Tyr Glu Glu Ala Met Ser Val Ser Leu Lys Lys Val Ser Gly
                660                 665                 670 ata aag gaa gaa att aaa gag cct gaa aat att aat gca gct ctt caa         2064
Ile Lys Glu Glu Ile Lys Glu Pro Glu Asn Ile Asn Ala Ala Leu Gln
                675                 680                 685 gaa aca gaa gct cct tat ata tct att gca tgt gat tta att aaa gaa         2112
Glu Thr Glu Ala Pro Tyr Ile Ser Ile Ala Cys Asp Leu Ile Lys Glu
            690                 695                 700 aca aag ctt tct gct gaa cca gct ccg gat ttc tct gat tat tca gaa         2160
Thr Lys Leu Ser Ala Glu Pro Ala Pro Asp Phe Ser Asp Tyr Ser Glu
705                 710                 715                 720 atg gca aaa gtt gaa cag cca gtg cct gat cat tct gag cta gtt gaa         2208
Met Ala Lys Val Glu Gln Pro Val Pro Asp His Ser Glu Leu Val Glu
                725                 730                 735 gat tcc tca cct gat tct gaa cca gtt gac tta ttt agt gat gat tca         2256
Asp Ser Ser Pro Asp Ser Glu Pro Val Asp Leu Phe Ser Asp Asp Ser
                740                 745                 750 ata cct gac gtt cca caa aaa caa gat gaa act gtg atg ctt gtg aaa         2304
Ile Pro Asp Val Pro Gln Lys Gln Asp Glu Thr Val Met Leu Val Lys
                755                 760                 765 gaa agt ctc act gag act tca ttt gag tca atg ata gaa tat gaa aat         2352
Glu Ser Leu Thr Glu Thr Ser Phe Glu Ser Met Ile Glu Tyr Glu Asn
770                 775                 780 aag gaa aaa ctc agt gct ttg cca cct gag gga gga aag cca tat ttg         2400
Lys Glu Lys Leu Ser Ala Leu Pro Pro Glu Gly Gly Lys Pro Tyr Leu
785                 790                 795                 800 gaa tct ttt aag ctc agt tta gat aac aca aaa gat acc ctg tta cct         2448
Glu Ser Phe Lys Leu Ser Leu Asp Asn Thr Lys Asp Thr Leu Leu Pro
                805                 810                 815 gat gaa gtt tca aca ttg agc aaa aag gag aaa att cct ttg cag atg         2496
Asp Glu Val Ser Thr Leu Ser Lys Lys Glu Lys Ile Pro Leu Gln Met
                820                 825                 830 gag gag ctc agt act gca gtt tat tca aat gat gac tta ttt att tct         2544
Glu Glu Leu Ser Thr Ala Val Tyr Ser Asn Asp Asp Leu Phe Ile Ser
                835                 840                 845 aag gaa gca cag ata aga gaa act gaa acg ttt tca gat tca tct cca         2592
Lys Glu Ala Gln Ile Arg Glu Thr Glu Thr Phe Ser Asp Ser Ser Pro
850                 855                 860 att gaa att ata gat gag ttc cct aca ttg atc agt tct aaa act gat         2640
Ile Glu Ile Ile Asp Glu Phe Pro Thr Leu Ile Ser Ser Lys Thr Asp
865                 870                 875                 880 tca ttt tct aaa tta gcc agg gaa tat act gac cta gaa gta tcc cac         2688
Ser Phe Ser Lys Leu Ala Arg Glu Tyr Thr Asp Leu Glu Val Ser His
                885                 890                 895 aaa agt gaa att gct aat gcc ccg gat gga gct ggg tca ttg cct tgc         2736
Lys Ser Glu Ile Ala Asn Ala Pro Asp Gly Ala Gly Ser Leu Pro Cys
                900                 905                 910 aca gaa ttg ccc cat gac ctt tct ttg aag aac ata caa ccc aaa gtt         2784
Thr Glu Leu Pro His Asp Leu Ser Leu Lys Asn Ile Gln Pro Lys Val
                915                 920                 925 gaa gag aaa atc agt ttc tca gat gac ttt tct aaa aat ggg tct gct         2832
Glu Glu Lys Ile Ser Phe Ser Asp Asp Phe Ser Lys Asn Gly Ser Ala
            930                 935                 940 aca tca aag gtg ctc tta ttg cct cca gat gtt tct gct ttg gcc act         2880
```

```
               Thr Ser Lys Val Leu Leu Pro Pro Asp Val Ser Ala Leu Ala Thr
               945                 950                 955                 960 caa gca gag ata gag agc ata gtt aaa ccc aaa gtt ctt gtg aaa gaa              2928
Gln Ala Glu Ile Glu Ser Ile Val Lys Pro Lys Val Leu Val Lys Glu
                965                 970                 975 gct gag aaa aaa ctt cct tcc gat aca gaa aaa gag gac aga tca cca              2976
Ala Glu Lys Lys Leu Pro Ser Asp Thr Glu Lys Glu Asp Arg Ser Pro
            980                 985                 990 tct gct ata ttt tca gca gag ctg  agt aaa act tca gtt  gtt gac ctc            3024
Ser Ala Ile Phe Ser Ala Glu Leu  Ser Lys Thr Ser Val  Val Asp Leu
        995                 1000                 1005 ctg tac tgg aga gac att aag  aag act gga gtg gtg  ttt ggt gcc                3069
Leu Tyr Trp Arg Asp Ile Lys  Lys Thr Gly Val Val  Phe Gly Ala
        1010                 1015                 1020 agc cta ttc ctg ctg ctt tca  ttg aca gta ttc agc  att gtg agc                3114
Ser Leu Phe Leu Leu Leu Ser  Leu Thr Val Phe Ser  Ile Val Ser
        1025                 1030                 1035 gta aca gcc tac att gcc ttg  gcc ctg ctc tct gtg  acc atc agc                3159
Val Thr Ala Tyr Ile Ala Leu  Ala Leu Leu Ser Val  Thr Ile Ser
        1040                 1045                 1050 ttt agg ata tac aag ggt gtg  atc caa gct atc cag  aaa tca gat                3204
Phe Arg Ile Tyr Lys Gly Val  Ile Gln Ala Ile Gln  Lys Ser Asp
        1055                 1060                 1065 gaa ggc cac cca ttc agg gca  tat ctg gaa tct gaa  gtt gct ata                3249
Glu Gly His Pro Phe Arg Ala  Tyr Leu Glu Ser Glu  Val Ala Ile
        1070                 1075                 1080 tct gag gag ttg gtt cag aag  tac agt aat tct gct  ctt ggt cat                3294
Ser Glu Glu Leu Val Gln Lys  Tyr Ser Asn Ser Ala  Leu Gly His
        1085                 1090                 1095 gtg aac tgc acg ata aag gaa  ctc agg cgc ctc ttc  tta gtt gat                3339
Val Asn Cys Thr Ile Lys Glu  Leu Arg Arg Leu Phe  Leu Val Asp
        1100                 1105                 1110 gat tta gtt gat tct ctg aag  ttt gca gtg ttg atg  tgg gta ttt                3384
Asp Leu Val Asp Ser Leu Lys  Phe Ala Val Leu Met  Trp Val Phe
        1115                 1120                 1125 acc tat gtt ggt gcc ttg ttt  aat ggt ctg aca cta  ctg att ttg                3429
Thr Tyr Val Gly Ala Leu Phe  Asn Gly Leu Thr Leu  Leu Ile Leu
        1130                 1135                 1140 gct ctc att tca ctc ttc agt  gtt cct gtt att tat  gaa cgg cat                3474
Ala Leu Ile Ser Leu Phe Ser  Val Pro Val Ile Tyr  Glu Arg His
        1145                 1150                 1155 cag gca cag ata gat cat tat  cta gga ctt gca aat  aag aat gtt                3519
Gln Ala Gln Ile Asp His Tyr  Leu Gly Leu Ala Asn  Lys Asn Val
        1160                 1165                 1170 aaa gat gct atg gct aaa atc  caa gca aaa atc cct  gga ttg aag                3564
Lys Asp Ala Met Ala Lys Ile  Gln Ala Lys Ile Pro  Gly Leu Lys
        1175                 1180                 1185 cgc aaa gct gaa tga aaacgcccaa ataattagt aggagttcat ctttaaggg                3619
Arg Lys Ala Glu
        1190 gatattcatt tgattatacg ggggagggtc agggaagaac gaaccttgac gttgcagtgc            3679 agtttcacag atcgttgtta gatctttatt tttagccatg cactgttgtg aggaaaaatt            3739 acctgtcttg actgccatgt gttcatcatc ttaagtattg taagctgcta tgtatggatt            3799 taaaccgtaa tcatatcttt ttcctatctg aggcactggt ggaataaaaa acctgtatat            3859 tttactttgt tgcagatagt cttgccgcat cttggcaagt tgcagagatg gtggagctag            3919
```

<210> SEQ ID NO 5

<211> LENGTH: 1192
<212> TYPE: PRT
<213> ORGANISM: Homo sapiens

<400> SEQUENCE: 5

```
Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro
            20                  25                  30

Asp Glu Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
                115                 120                 125

Ser Pro Ser Lys Leu Pro Glu Asp Asp Glu Pro Pro Ala Arg Pro Pro
130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
                180                 185                 190

Pro Ala Ala Ser Glu Pro Val Ile Arg Ser Ser Ala Glu Asn Met Asp
                195                 200                 205

Leu Lys Glu Gln Pro Gly Asn Thr Ile Ser Ala Gly Gln Glu Asp Phe
210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
                260                 265                 270

Ser Lys Glu Val Ser Glu Lys Ala Lys Thr Leu Leu Ile Asp Arg Asp
275                 280                 285

Leu Thr Glu Phe Ser Glu Leu Glu Tyr Ser Glu Met Gly Ser Ser Phe
290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Lys Leu Val Ser
                325                 330                 335

Asn Asn Ile Leu His Asn Gln Gln Glu Leu Pro Thr Ala Leu Thr Lys
                340                 345                 350

Leu Val Lys Glu Asp Glu Val Val Ser Ser Lys Ala Lys Asp Ser
                355                 360                 365

Phe Asn Glu Lys Arg Val Ala Val Glu Ala Pro Met Arg Glu Glu Tyr
                370                 375                 380

Ala Asp Phe Lys Pro Phe Glu Arg Val Trp Glu Val Lys Asp Ser Lys
```

-continued

```
        385                 390                 395                 400
Glu Asp Ser Asp Met Leu Ala Ala Gly Gly Lys Ile Glu Ser Asn Leu
                405                 410                 415
Glu Ser Lys Val Asp Lys Lys Cys Phe Ala Asp Ser Leu Glu Gln Thr
                420                 425                 430
Asn His Glu Lys Asp Ser Glu Ser Ser Asn Asp Asp Thr Ser Phe Pro
                435                 440                 445
Ser Thr Pro Glu Gly Ile Lys Asp Arg Ser Gly Ala Tyr Ile Thr Cys
        450                 455                 460
Ala Pro Phe Asn Pro Ala Ala Thr Glu Ser Ile Ala Thr Asn Ile Phe
465                 470                 475                 480
Pro Leu Leu Gly Asp Pro Thr Ser Glu Asn Lys Thr Asp Glu Lys Lys
                485                 490                 495
Ile Glu Glu Lys Lys Ala Gln Ile Val Thr Glu Lys Asn Thr Ser Thr
                500                 505                 510
Lys Thr Ser Asn Pro Phe Leu Val Ala Ala Gln Asp Ser Glu Thr Asp
                515                 520                 525
Tyr Val Thr Thr Asp Asn Leu Thr Lys Val Thr Glu Glu Val Val Ala
        530                 535                 540
Asn Met Pro Glu Gly Leu Thr Pro Asp Leu Val Gln Glu Ala Cys Glu
545                 550                 555                 560
Ser Glu Leu Asn Glu Val Thr Gly Thr Lys Ile Ala Tyr Glu Thr Lys
                565                 570                 575
Met Asp Leu Val Gln Thr Ser Glu Val Met Gln Glu Ser Leu Tyr Pro
                580                 585                 590
Ala Ala Gln Leu Cys Pro Ser Phe Glu Glu Ser Glu Ala Thr Pro Ser
                595                 600                 605
Pro Val Leu Pro Asp Ile Val Met Glu Ala Pro Leu Asn Ser Ala Val
        610                 615                 620
Pro Ser Ala Gly Ala Ser Val Ile Gln Pro Ser Ser Ser Pro Leu Glu
625                 630                 635                 640
Ala Ser Ser Val Asn Tyr Glu Ser Ile Lys His Glu Pro Glu Asn Pro
                645                 650                 655
Pro Pro Tyr Glu Glu Ala Met Ser Val Ser Leu Lys Lys Val Ser Gly
                660                 665                 670
Ile Lys Glu Glu Ile Lys Glu Pro Glu Asn Ile Asn Ala Ala Leu Gln
        675                 680                 685
Glu Thr Glu Ala Pro Tyr Ile Ser Ile Ala Cys Asp Leu Ile Lys Glu
        690                 695                 700
Thr Lys Leu Ser Ala Glu Pro Ala Pro Asp Phe Ser Asp Tyr Ser Glu
705                 710                 715                 720
Met Ala Lys Val Glu Gln Pro Val Pro Asp His Ser Glu Leu Val Glu
                725                 730                 735
Asp Ser Ser Pro Asp Ser Glu Pro Val Asp Leu Phe Ser Asp Asp Ser
                740                 745                 750
Ile Pro Asp Val Pro Gln Lys Gln Asp Glu Thr Val Met Leu Val Lys
                755                 760                 765
Glu Ser Leu Thr Glu Thr Ser Phe Glu Ser Met Ile Glu Tyr Glu Asn
                770                 775                 780
Lys Glu Lys Leu Ser Ala Leu Pro Pro Glu Gly Gly Lys Pro Tyr Leu
785                 790                 795                 800
Glu Ser Phe Lys Leu Ser Leu Asp Asn Thr Lys Asp Thr Leu Leu Pro
                805                 810                 815
```

```
Asp Glu Val Ser Thr Leu Ser Lys Lys Glu Lys Ile Pro Leu Gln Met
        820                 825                 830

Glu Glu Leu Ser Thr Ala Val Tyr Ser Asn Asp Asp Leu Phe Ile Ser
        835                 840                 845

Lys Glu Ala Gln Ile Arg Glu Thr Glu Thr Phe Ser Asp Ser Ser Pro
    850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
            885                 890                 895

Lys Ser Glu Ile Ala Asn Ala Pro Asp Gly Ala Gly Ser Leu Pro Cys
        900                 905                 910

Thr Glu Leu Pro His Asp Leu Ser Leu Lys Asn Ile Gln Pro Lys Val
            915                 920                 925

Glu Glu Lys Ile Ser Phe Ser Asp Asp Phe Ser Lys Asn Gly Ser Ala
    930                 935                 940

Thr Ser Lys Val Leu Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
            965                 970                 975

Ala Glu Lys Lys Leu Pro Ser Asp Thr Glu Lys Glu Asp Arg Ser Pro
        980                 985                 990

Ser Ala Ile Phe Ser Ala Glu Leu  Ser Lys Thr Ser Val  Val Asp Leu
            995                 1000                1005

Leu Tyr  Trp Arg Asp Ile Lys  Lys Thr Gly Val Val  Phe Gly Ala
    1010                1015                1020

Ser Leu  Phe Leu Leu Leu Ser  Leu Thr Val Phe Ser  Ile Val Ser
    1025                1030                1035

Val Thr  Ala Tyr Ile Ala Leu  Ala Leu Leu Ser Val  Thr Ile Ser
    1040                1045                1050

Phe Arg  Ile Tyr Lys Gly Val  Ile Gln Ala Ile Gln  Lys Ser Asp
    1055                1060                1065

Glu Gly  His Pro Phe Arg Ala  Tyr Leu Glu Ser Glu  Val Ala Ile
    1070                1075                1080

Ser Glu  Glu Leu Val Gln Lys  Tyr Ser Asn Ser Ala  Leu Gly His
    1085                1090                1095

Val Asn  Cys Thr Ile Lys Glu  Leu Arg Arg Leu Phe  Leu Val Asp
    1100                1105                1110

Asp Leu  Val Asp Ser Leu Lys  Phe Ala Val Leu Met  Trp Val Phe
    1115                1120                1125

Thr Tyr  Val Gly Ala Leu Phe  Asn Gly Leu Thr Leu  Leu Ile Leu
    1130                1135                1140

Ala Leu  Ile Ser Leu Phe Ser  Val Pro Val Ile Tyr  Glu Arg His
    1145                1150                1155

Gln Ala  Gln Ile Asp His Tyr  Leu Gly Leu Ala Asn  Lys Asn Val
    1160                1165                1170

Lys Asp  Ala Met Ala Lys Ile  Gln Ala Lys Ile Pro  Gly Leu Lys
    1175                1180                1185

Arg Lys  Ala Glu
    1190

<210> SEQ ID NO 6
<211> LENGTH: 18
```

```
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Human NogoA_623-640

<400> SEQUENCE: 6

Asn Tyr Glu Ser Ile Lys His Glu Pro Glu Asn Pro Pro Tyr Glu
1               5                   10                  15

Glu Ala

<210> SEQ ID NO 7
<211> LENGTH: 819
<212> TYPE: PRT
<213> ORGANISM: Homo sapiens
<220> FEATURE:
<221> NAME/KEY: PEPTIDE
<222> LOCATION: (1)..(819)
<223> OTHER INFORMATION: human Nig

<400> SEQUENCE: 7

Asp Glu Thr Leu Phe Ala Leu Pro Ala Ala Ser Glu Pro Val Ile Arg
1               5                   10                  15

Ser Ser Ala Glu Asn Met Asp Leu Lys Glu Gln Pro Gly Asn Thr Ile
                20                  25                  30

Ser Ala Gly Gln Glu Asp Phe Pro Ser Val Leu Leu Glu Thr Ala Ala
            35                  40                  45

Ser Leu Pro Ser Leu Ser Pro Leu Ser Ala Ala Ser Phe Lys Glu His
        50                  55                  60

Glu Tyr Leu Gly Asn Leu Ser Thr Val Leu Pro Thr Glu Gly Thr Leu
65                  70                  75                  80

Gln Glu Asn Val Ser Glu Ala Ser Lys Glu Val Ser Glu Lys Ala Lys
                85                  90                  95

Thr Leu Leu Ile Asp Arg Asp Leu Thr Glu Phe Ser Glu Leu Glu Tyr
            100                 105                 110

Ser Glu Met Gly Ser Ser Phe Ser Val Ser Pro Lys Ala Glu Ser Ala
        115                 120                 125

Val Ile Val Ala Asn Pro Arg Glu Glu Ile Ile Val Lys Asn Lys Asp
130                 135                 140

Glu Glu Glu Lys Leu Val Ser Asn Asn Ile Leu His Asn Gln Gln Glu
145                 150                 155                 160

Leu Pro Thr Ala Leu Thr Lys Leu Val Lys Glu Asp Glu Val Val Ser
                165                 170                 175

Ser Glu Lys Ala Lys Asp Ser Phe Asn Glu Lys Arg Val Ala Val Glu
            180                 185                 190

Ala Pro Met Arg Glu Glu Tyr Ala Asp Phe Lys Pro Phe Glu Arg Val
        195                 200                 205

Trp Glu Val Lys Asp Ser Lys Glu Asp Ser Asp Met Leu Ala Ala Gly
        210                 215                 220

Gly Lys Ile Glu Ser Asn Leu Glu Ser Lys Val Asp Lys Lys Cys Phe
225                 230                 235                 240

Ala Asp Ser Leu Glu Gln Thr Asn His Glu Lys Asp Ser Glu Ser Ser
                245                 250                 255

Asn Asp Asp Thr Ser Phe Pro Ser Thr Pro Glu Gly Ile Lys Asp Arg
            260                 265                 270

Ser Gly Ala Tyr Ile Thr Cys Ala Pro Phe Asn Pro Ala Ala Thr Glu
        275                 280                 285
```

```
Ser Ile Ala Thr Asn Ile Phe Pro Leu Leu Gly Asp Pro Thr Ser Glu
    290                 295                 300
Asn Lys Thr Asp Glu Lys Ile Glu Lys Lys Ala Gln Ile Val
305                 310                 315                 320
Thr Glu Lys Asn Thr Ser Thr Lys Thr Ser Asn Pro Phe Leu Val Ala
                325                 330                 335
Ala Gln Asp Ser Glu Thr Asp Tyr Val Thr Thr Asp Asn Leu Thr Lys
                340                 345                 350
Val Thr Glu Glu Val Val Ala Asn Met Pro Glu Gly Leu Thr Pro Asp
            355                 360                 365
Leu Val Gln Glu Ala Cys Glu Ser Glu Leu Asn Glu Val Thr Gly Thr
    370                 375                 380
Lys Ile Ala Tyr Glu Thr Lys Met Asp Leu Val Gln Thr Ser Glu Val
385                 390                 395                 400
Met Gln Glu Ser Leu Tyr Pro Ala Ala Gln Leu Cys Pro Ser Phe Glu
                405                 410                 415
Glu Ser Glu Ala Thr Pro Ser Pro Val Leu Pro Asp Ile Val Met Glu
            420                 425                 430
Ala Pro Leu Asn Ser Ala Val Pro Ser Ala Gly Ala Ser Val Ile Gln
    435                 440                 445
Pro Ser Ser Ser Pro Leu Glu Ala Ser Ser Val Asn Tyr Glu Ser Ile
    450                 455                 460
Lys His Glu Pro Glu Asn Pro Pro Tyr Glu Glu Ala Met Ser Val
465                 470                 475                 480
Ser Leu Lys Lys Val Ser Gly Ile Lys Glu Glu Ile Lys Glu Pro Glu
                485                 490                 495
Asn Ile Asn Ala Ala Leu Gln Glu Thr Glu Ala Pro Tyr Ile Ser Ile
            500                 505                 510
Ala Cys Asp Leu Ile Lys Glu Thr Lys Leu Ser Ala Glu Pro Ala Pro
    515                 520                 525
Asp Phe Ser Asp Tyr Ser Glu Met Ala Lys Val Glu Gln Pro Val Pro
    530                 535                 540
Asp His Ser Glu Leu Val Glu Asp Ser Ser Pro Asp Ser Glu Pro Val
545                 550                 555                 560
Asp Leu Phe Ser Asp Asp Ser Ile Pro Asp Val Pro Gln Lys Gln Asp
                565                 570                 575
Glu Thr Val Met Leu Val Lys Glu Ser Leu Thr Glu Thr Ser Phe Glu
            580                 585                 590
Ser Met Ile Glu Tyr Glu Asn Lys Glu Lys Leu Ser Ala Leu Pro Pro
    595                 600                 605
Glu Gly Gly Lys Pro Tyr Leu Glu Ser Phe Lys Leu Ser Leu Asp Asn
    610                 615                 620
Thr Lys Asp Thr Leu Leu Pro Asp Glu Val Ser Thr Leu Ser Lys Lys
625                 630                 635                 640
Glu Lys Ile Pro Leu Gln Met Glu Glu Leu Ser Thr Ala Val Tyr Ser
                645                 650                 655
Asn Asp Asp Leu Phe Ile Ser Lys Glu Ala Gln Ile Arg Glu Thr Glu
            660                 665                 670
Thr Phe Ser Asp Ser Ser Pro Ile Glu Ile Asp Glu Phe Pro Thr
    675                 680                 685
Leu Ile Ser Ser Lys Thr Asp Ser Phe Ser Lys Leu Ala Arg Glu Tyr
    690                 695                 700
```

-continued

```
Thr Asp Leu Glu Val Ser His Lys Ser Glu Ile Ala Asn Ala Pro Asp
705                 710                 715                 720

Gly Ala Gly Ser Leu Pro Cys Thr Glu Leu Pro His Asp Leu Ser Leu
                725                 730                 735

Lys Asn Ile Gln Pro Lys Val Glu Lys Ile Ser Phe Ser Asp Asp
            740                 745                 750

Phe Ser Lys Asn Gly Ser Ala Thr Ser Lys Val Leu Leu Leu Pro Pro
        755                 760                 765

Asp Val Ser Ala Leu Ala Thr Gln Ala Glu Ile Glu Ser Ile Val Lys
        770                 775                 780

Pro Lys Val Leu Val Lys Glu Ala Glu Lys Lys Leu Pro Ser Asp Thr
785                 790                 795                 800

Glu Lys Glu Asp Arg Ser Pro Ser Ala Ile Phe Ser Ala Glu Leu Ser
                805                 810                 815

Lys Thr Ser

<210> SEQ ID NO 8
<211> LENGTH: 10
<212> TYPE: PRT
<213> ORGANISM: Mus musculus
<220> FEATURE:
<221> NAME/KEY: BINDING
<222> LOCATION: (1)..(10)
<223> OTHER INFORMATION: hypervariable part of heavy chain of 11C7

<400> SEQUENCE: 8

Gly Phe Asp Phe Arg Arg Asn Trp Met Ser
1               5                   10

<210> SEQ ID NO 9
<211> LENGTH: 17
<212> TYPE: PRT
<213> ORGANISM: Mus musculus
<220> FEATURE:
<221> NAME/KEY: BINDING
<222> LOCATION: (1)..(17)
<223> OTHER INFORMATION: hypervariable part of heavy chain of 11C7

<400> SEQUENCE: 9

Glu Ile Asn Pro Asp Ser Ser Lys Ile Asn Tyr Thr Pro Ser Leu Lys
1               5                   10                  15

Asp

<210> SEQ ID NO 10
<211> LENGTH: 9
<212> TYPE: PRT
<213> ORGANISM: Mus musculus
<220> FEATURE:
<221> NAME/KEY: BINDING
<222> LOCATION: (1)..(9)
<223> OTHER INFORMATION: hypervariable part of heavy chain of 11C7

<400> SEQUENCE: 10

Pro Val Trp Met Tyr Ala Met Asp Tyr
1               5

<210> SEQ ID NO 11
<211> LENGTH: 16
<212> TYPE: PRT
<213> ORGANISM: Mus musculus
<220> FEATURE:
<221> NAME/KEY: BINDING
<222> LOCATION: (1)..(16)
<223> OTHER INFORMATION: hypervariable part of light chain of 11C7
```

```
<400> SEQUENCE: 11

Lys Ser Ser Gln Ser Leu Leu His Ser Asp Gly Lys Thr Tyr Leu Asn
1               5                   10                  15

<210> SEQ ID NO 12
<211> LENGTH: 7
<212> TYPE: PRT
<213> ORGANISM: Mus musculus
<220> FEATURE:
<221> NAME/KEY: BINDING
<222> LOCATION: (1)..(7)
<223> OTHER INFORMATION: hypervariable part of light chain of 11C7

<400> SEQUENCE: 12

Leu Val Ser Lys Leu Asp Ser
1               5

<210> SEQ ID NO 13
<211> LENGTH: 9
<212> TYPE: PRT
<213> ORGANISM: Mus musculus
<220> FEATURE:
<221> NAME/KEY: BINDING
<222> LOCATION: (1)..(9)
<223> OTHER INFORMATION: hypervariable part of light chain of 11C7

<400> SEQUENCE: 13

Trp Gln Gly Thr His Phe Pro Gln Thr
1               5

<210> SEQ ID NO 14
<211> LENGTH: 30
<212> TYPE: DNA
<213> ORGANISM: Mus musculus
<220> FEATURE:
<221> NAME/KEY: misc_binding
<222> LOCATION: (1)..(30)
<223> OTHER INFORMATION: DNA-CDR1-11C7

<400> SEQUENCE: 14
ggattcgatt ttagaagaaa ttggatgagt                                     30

<210> SEQ ID NO 15
<211> LENGTH: 51
<212> TYPE: DNA
<213> ORGANISM: Mus musculus
<220> FEATURE:
<221> NAME/KEY: misc_binding
<222> LOCATION: (1)..(51)
<223> OTHER INFORMATION: DNA-CDR2-11C7

<400> SEQUENCE: 15
gaaattaatc cagatagcag taagataaac tatacgccat ctctaaagga t             51

<210> SEQ ID NO 16
<211> LENGTH: 27
<212> TYPE: DNA
<213> ORGANISM: Mus musculus
<220> FEATURE:
<221> NAME/KEY: misc_binding
<222> LOCATION: (1)..(27)
<223> OTHER INFORMATION: DNA-CDR3-11C7

<400> SEQUENCE: 16
ccggtctgga tgtatgctat ggactac                                        27
```

```
<210> SEQ ID NO 17
<211> LENGTH: 48
<212> TYPE: DNA
<213> ORGANISM: Mus musculus
<220> FEATURE:
<221> NAME/KEY: misc_binding
<222> LOCATION: (1)..(48)
<223> OTHER INFORMATION: DNA-CDR'1-11C7

<400> SEQUENCE: 17
aagtcaagtc agagcctctt gcatagtgat ggaaagacat atttgaat                    48

<210> SEQ ID NO 18
<211> LENGTH: 21
<212> TYPE: DNA
<213> ORGANISM: Mus musculus
<220> FEATURE:
<221> NAME/KEY: misc_binding
<222> LOCATION: (1)..(21)
<223> OTHER INFORMATION: DNA-CDR'2-11C7

<400> SEQUENCE: 18
ctggtgtcta aactggactc t                                                 21

<210> SEQ ID NO 19
<211> LENGTH: 27
<212> TYPE: DNA
<213> ORGANISM: Mus musculus
<220> FEATURE:
<221> NAME/KEY: misc_binding
<222> LOCATION: (1)..(27)
<223> OTHER INFORMATION: DNA-CDR'3-11C7

<400> SEQUENCE: 19
tggcaaggta cacatttttcc tcagacg                                          27

<210> SEQ ID NO 20
<211> LENGTH: 54
<212> TYPE: DNA
<213> ORGANISM: Mus musculus
<220> FEATURE:
<221> NAME/KEY: CDS
<222> LOCATION: (1)..(54)
<223> OTHER INFORMATION: leader sequence for heavy chain of 11C7

<400> SEQUENCE: 20 atg gat ttt ggg ctg att ttt ttt att gtt ggt ctt tta aaa ggg gtc         48
Met Asp Phe Gly Leu Ile Phe Phe Ile Val Gly Leu Leu Lys Gly Val
1               5                   10                  15 cag tgt                                                                 54
Gln Cys <210> SEQ ID NO 21
<211> LENGTH: 18
<212> TYPE: PRT
<213> ORGANISM: Mus musculus

<400> SEQUENCE: 21

Met Asp Phe Gly Leu Ile Phe Phe Ile Val Gly Leu Leu Lys Gly Val
1               5                   10                  15

Gln Cys

<210> SEQ ID NO 22
<211> LENGTH: 57
<212> TYPE: DNA
<213> ORGANISM: Mus musculus
<220> FEATURE:
```

-continued

```
<221> NAME/KEY: CDS
<222> LOCATION: (1)..(57)
<223> OTHER INFORMATION: leader sequence for 11C7-light chain

<400> SEQUENCE: 22 atg agt cct gcc cag ttc ctg ttt ctg tta gtg ctc tgg att cgg gaa      48
Met Ser Pro Ala Gln Phe Leu Phe Leu Leu Val Leu Trp Ile Arg Glu
1               5                   10                  15 acc agc ggt                                                          57
Thr Ser Gly <210> SEQ ID NO 23
<211> LENGTH: 19
<212> TYPE: PRT
<213> ORGANISM: Mus musculus

<400> SEQUENCE: 23

Met Ser Pro Ala Gln Phe Leu Phe Leu Leu Val Leu Trp Ile Arg Glu
1               5                   10                  15

Thr Ser Gly

<210> SEQ ID NO 24
<211> LENGTH: 181
<212> TYPE: PRT
<213> ORGANISM: Homo sapiens
<220> FEATURE:
<221> NAME/KEY: PEPTIDE
<222> LOCATION: (1)..(181)
<223> OTHER INFORMATION: human Nig-D20

<400> SEQUENCE: 24

Gly Thr Lys Ile Ala Tyr Glu Thr Lys Met Asp Leu Val Gln Thr Ser
1               5                   10                  15

Glu Val Met Gln Glu Ser Leu Tyr Pro Ala Ala Gln Leu Cys Pro Ser
                20                  25                  30

Phe Glu Glu Ser Glu Ala Thr Pro Ser Pro Val Leu Pro Asp Ile Val
            35                  40                  45

Met Glu Ala Pro Leu Asn Ser Ala Val Pro Ser Ala Gly Ala Ser Val
        50                  55                  60

Ile Gln Pro Ser Ser Pro Leu Glu Ala Ser Ser Val Asn Tyr Glu
65                  70                  75                  80

Ser Ile Lys His Glu Pro Glu Asn Pro Pro Tyr Glu Glu Ala Met
                85                  90                  95

Ser Val Ser Leu Lys Lys Val Ser Gly Ile Lys Glu Glu Ile Lys Glu
                100                 105                 110

Pro Glu Asn Ile Asn Ala Ala Leu Gln Glu Thr Glu Ala Pro Tyr Ile
            115                 120                 125

Ser Ile Ala Cys Asp Leu Ile Lys Glu Thr Lys Leu Ser Ala Glu Pro
        130                 135                 140

Ala Pro Asp Phe Ser Asp Tyr Ser Glu Met Ala Lys Val Glu Gln Pro
145                 150                 155                 160

Val Pro Asp His Ser Glu Leu Val Glu Asp Ser Ser Pro Asp Ser Glu
                165                 170                 175

Pro Val Asp Leu Phe
            180

<210> SEQ ID NO 25
<211> LENGTH: 3492
<212> TYPE: DNA
<213> ORGANISM: Rattus norvegicus
```

<220> FEATURE:
<221> NAME/KEY: CDS
<222> LOCATION: (1)..(3492)
<223> OTHER INFORMATION: rat NogoA

<400> SEQUENCE: 25

```
atg gaa gac ata gac cag tcg tcg ctg gtc tcc tcg tcc acg gac agc      48
Met Glu Asp Ile Asp Gln Ser Ser Leu Val Ser Ser Ser Thr Asp Ser
1               5                   10                  15 ccg ccc cgg cct ccg ccc gcc ttc aag tac cag ttc gtg acg gag ccc      96
Pro Pro Arg Pro Pro Pro Ala Phe Lys Tyr Gln Phe Val Thr Glu Pro
            20                  25                  30 gag gac gag gag gac gag gag gag gag gac gag gag gag gac gac         144
Glu Asp Glu Glu Asp Glu Glu Glu Glu Asp Glu Glu Glu Asp Asp
        35                  40                  45 gag gac cta gag gaa ctg gag gtg ctg gag agg aag ccc gca gcc ggg     192
Glu Asp Leu Glu Glu Leu Glu Val Leu Glu Arg Lys Pro Ala Ala Gly
    50                  55                  60 ctg tcc gca gct gcg gtg ccg ccc gcc gcc gcg ccg ctg ctg gac         240
Leu Ser Ala Ala Ala Val Pro Pro Ala Ala Ala Pro Leu Leu Asp
65                  70                  75                  80 ttc agc agc gac tcg gtg ccc ccc gcg ccc cgc ggg ccg ctg ccg gcc     288
Phe Ser Ser Asp Ser Val Pro Pro Ala Pro Arg Gly Pro Leu Pro Ala
                85                  90                  95 gcg ccc cct gcc gct cct gag agg cag cca tcc tgg gaa cgc agc ccc     336
Ala Pro Pro Ala Ala Pro Glu Arg Gln Pro Ser Trp Glu Arg Ser Pro
            100                 105                 110 gcg gcg ccc gcg cca tcc ctg ccg ccc gct gcc gca gtc ctg ccc tcc     384
Ala Ala Pro Ala Pro Ser Leu Pro Pro Ala Ala Ala Val Leu Pro Ser
        115                 120                 125 aag ctc cca gag gac gac gag cct ccg gcg agg ccc ccg cct ccg ccg     432
Lys Leu Pro Glu Asp Asp Glu Pro Pro Ala Arg Pro Pro Pro Pro
    130                 135                 140 cca gcc ggc gca agc ccc ctg gcg gag ccc gcc gcg ccc cct tcc acg     480
Pro Ala Gly Ala Ser Pro Leu Ala Glu Pro Ala Ala Pro Pro Ser Thr
145                 150                 155                 160 ccg gcc gcg ccc aag cgc agg ggc tcc ggc tca gtg gat gag acc ctt     528
Pro Ala Ala Pro Lys Arg Arg Gly Ser Gly Ser Val Asp Glu Thr Leu
                165                 170                 175 ttt gct ctt cct gct gca tct gag cct gtg ata ccc tcc tct gca gaa     576
Phe Ala Leu Pro Ala Ala Ser Glu Pro Val Ile Pro Ser Ser Ala Glu
            180                 185                 190 aaa att atg gat ttg atg gag cag cca ggt aac act gtt tcg tct ggt     624
Lys Ile Met Asp Leu Met Glu Gln Pro Gly Asn Thr Val Ser Ser Gly
        195                 200                 205 caa gag gat ttc cca tct gtc ctg ctt gaa act gct gcc tct ctt cct     672
Gln Glu Asp Phe Pro Ser Val Leu Leu Glu Thr Ala Ala Ser Leu Pro
    210                 215                 220 tct cta tct cct ctc tca act gtt tct ttt aaa gaa cat gga tac ctt     720
Ser Leu Ser Pro Leu Ser Thr Val Ser Phe Lys Glu His Gly Tyr Leu
225                 230                 235                 240 ggt aac tta tca gca gtg tca tcc tca gaa gga aca att gaa gaa act     768
Gly Asn Leu Ser Ala Val Ser Ser Ser Glu Gly Thr Ile Glu Glu Thr
                245                 250                 255 tta aat gaa gct tct aaa gag ttg cca gag agg gca aca aat cca ttt     816
Leu Asn Glu Ala Ser Lys Glu Leu Pro Glu Arg Ala Thr Asn Pro Phe
            260                 265                 270 gta aat aga gat tta gca gaa ttt tca gaa tta gaa tat tca gaa atg     864
Val Asn Arg Asp Leu Ala Glu Phe Ser Glu Leu Glu Tyr Ser Glu Met
        275                 280                 285
```

| | | |
|---|---|---|
| gga tca tct ttt aaa ggc tcc cca aaa gga gag tca gcc ata tta gta<br>Gly Ser Ser Phe Lys Gly Ser Pro Lys Gly Glu Ser Ala Ile Leu Val<br>290                        295                       300 | | 912 |
| gaa aac act aag gaa gaa gta att gtg agg agt aaa gac aaa gag gat<br>Glu Asn Thr Lys Glu Glu Val Ile Val Arg Ser Lys Asp Lys Glu Asp<br>305                     310                     315                    320 | | 960 |
| tta gtt tgt agt gca gcc ctt cac agt cca caa gaa tca cct gtg ggt<br>Leu Val Cys Ser Ala Ala Leu His Ser Pro Gln Glu Ser Pro Val Gly<br>                     325                     330                    335 | | 1008 |
| aaa gaa gac aga gtt gtg tct cca gaa aag aca atg gac att ttt aat<br>Lys Glu Asp Arg Val Val Ser Pro Glu Lys Thr Met Asp Ile Phe Asn<br>                 340                     345                    350 | | 1056 |
| gaa atg cag atg tca gta gta gca cct gtg agg gaa gag tat gca gac<br>Glu Met Gln Met Ser Val Val Ala Pro Val Arg Glu Glu Tyr Ala Asp<br>355                     360                     365 | | 1104 |
| ttt aag cca ttt gaa caa gca tgg gaa gtg aaa gat act tat gag gga<br>Phe Lys Pro Phe Glu Gln Ala Trp Glu Val Lys Asp Thr Tyr Glu Gly<br>370                     375                     380 | | 1152 |
| agt agg gat gtg ctg gct gct aga gct aat gtg gaa agt aaa gtg gac<br>Ser Arg Asp Val Leu Ala Ala Arg Ala Asn Val Glu Ser Lys Val Asp<br>385                     390                     395                    400 | | 1200 |
| aga aaa tgc ttg gaa gat agc ctg gag caa aaa agt ctt ggg aag gat<br>Arg Lys Cys Leu Glu Asp Ser Leu Glu Gln Lys Ser Leu Gly Lys Asp<br>                 405                     410                    415 | | 1248 |
| agt gaa ggc aga aat gag gat gct tct ttc ccc agt acc cca gaa cct<br>Ser Glu Gly Arg Asn Glu Asp Ala Ser Phe Pro Ser Thr Pro Glu Pro<br>                 420                     425                    430 | | 1296 |
| gtg aag gac agc tcc aga gca tat att acc tgt gct tcc ttt acc tca<br>Val Lys Asp Ser Ser Arg Ala Tyr Ile Thr Cys Ala Ser Phe Thr Ser<br>435                     440                     445 | | 1344 |
| gca acc gaa agc acc aca gca aac act ttc cct ttg tta gaa gat cat<br>Ala Thr Glu Ser Thr Thr Ala Asn Thr Phe Pro Leu Leu Glu Asp His<br>450                     455                     460 | | 1392 |
| act tca gaa aat aaa aca gat gaa aaa aaa ata gaa gaa agg aag gcc<br>Thr Ser Glu Asn Lys Thr Asp Glu Lys Lys Ile Glu Glu Arg Lys Ala<br>465                     470                     475                    480 | | 1440 |
| caa att ata aca gag aag act agc ccc aaa acg tca aat cct ttc ctt<br>Gln Ile Ile Thr Glu Lys Thr Ser Pro Lys Thr Ser Asn Pro Phe Leu<br>                 485                     490                    495 | | 1488 |
| gta gca gta cag gat tct gag gca gat tat gtt aca aca gat acc tta<br>Val Ala Val Gln Asp Ser Glu Ala Asp Tyr Val Thr Thr Asp Thr Leu<br>                 500                     505                    510 | | 1536 |
| tca aag gtg act gag gca gca gtg tca aac atg cct gaa ggt ctg acg<br>Ser Lys Val Thr Glu Ala Ala Val Ser Asn Met Pro Glu Gly Leu Thr<br>515                     520                     525 | | 1584 |
| cca gat tta gtt cag gaa gca tgt gaa agt gaa ctg aat gaa gcc aca<br>Pro Asp Leu Val Gln Glu Ala Cys Glu Ser Glu Leu Asn Glu Ala Thr<br>530                     535                     540 | | 1632 |
| ggt aca aag att gct tat gaa aca aaa gtg gac ttg gtc caa aca tca<br>Gly Thr Lys Ile Ala Tyr Glu Thr Lys Val Asp Leu Val Gln Thr Ser<br>545                     550                     555                    560 | | 1680 |
| gaa gct ata caa gaa tca ctt tac ccc aca gca cag ctt tgc cca tca<br>Glu Ala Ile Gln Glu Ser Leu Tyr Pro Thr Ala Gln Leu Cys Pro Ser<br>                 565                     570                    575 | | 1728 |
| ttt gag gaa gct gaa gca act ccg tca cca gtt tgc cct gat att gtt<br>Phe Glu Glu Ala Glu Ala Thr Pro Ser Pro Val Leu Pro Asp Ile Val<br>                 580                     585                    590 | | 1776 |
| atg gaa gca cca tta aat tct ctc ctt cca agc gct ggt gct tct gta<br>Met Glu Ala Pro Leu Asn Ser Leu Leu Pro Ser Ala Gly Ala Ser Val<br>595                     600                     605 | | 1824 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | cag | ccc | agt | gta | tcc | cca | ctg | gaa | gca | cct | cct | cca | gtt | agt | tat | 1872 |
| Val | Gln | Pro | Ser | Val | Ser | Pro | Leu | Glu | Ala | Pro | Pro | Pro | Val | Ser | Tyr |      |
|     | 610 |     |     |     | 615 |     |     |     |     | 620 |     |     |     |     |     |      |
| gac | agt | ata | aag | ctt | gag | cct | gaa | aac | ccc | cca | cca | tat | gaa | gaa | gcc | 1920 |
| Asp | Ser | Ile | Lys | Leu | Glu | Pro | Glu | Asn | Pro | Pro | Pro | Tyr | Glu | Glu | Ala |      |
| 625 |     |     |     |     | 630 |     |     |     |     | 635 |     |     |     |     | 640 |      |
| atg | aat | gta | gca | cta | aaa | gct | ttg | gga | aca | aag | gaa | gga | ata | aaa | gag | 1968 |
| Met | Asn | Val | Ala | Leu | Lys | Ala | Leu | Gly | Thr | Lys | Glu | Gly | Ile | Lys | Glu |      |
|     |     |     |     | 645 |     |     |     |     | 650 |     |     |     |     | 655 |     |      |
| cct | gaa | agt | ttt | aat | gca | gct | gtt | cag | gaa | aca | gaa | gct | cct | tat | ata | 2016 |
| Pro | Glu | Ser | Phe | Asn | Ala | Ala | Val | Gln | Glu | Thr | Glu | Ala | Pro | Tyr | Ile |      |
|     |     |     | 660 |     |     |     |     | 665 |     |     |     |     | 670 |     |     |      |
| tcc | att | gcg | tgt | gat | tta | att | aaa | gaa | aca | aag | ctc | tcc | act | gag | cca | 2064 |
| Ser | Ile | Ala | Cys | Asp | Leu | Ile | Lys | Glu | Thr | Lys | Leu | Ser | Thr | Glu | Pro |      |
|     |     | 675 |     |     |     |     | 680 |     |     |     |     | 685 |     |     |     |      |
| agt | cca | gat | ttc | tct | aat | tat | tca | gaa | ata | gca | aaa | ttc | gag | aag | tcg | 2112 |
| Ser | Pro | Asp | Phe | Ser | Asn | Tyr | Ser | Glu | Ile | Ala | Lys | Phe | Glu | Lys | Ser |      |
| 690 |     |     |     |     | 695 |     |     |     |     | 700 |     |     |     |     |     |      |
| gtg | ccc | gaa | cac | gct | gag | cta | gtg | gag | gat | tcc | tca | cct | gaa | tct | gaa | 2160 |
| Val | Pro | Glu | His | Ala | Glu | Leu | Val | Glu | Asp | Ser | Ser | Pro | Glu | Ser | Glu |      |
| 705 |     |     |     | 710 |     |     |     |     | 715 |     |     |     |     | 720 |     |      |
| cca | gtt | gac | tta | ttt | agt | gat | gat | tcg | att | cct | gaa | gtc | cca | caa | aca | 2208 |
| Pro | Val | Asp | Leu | Phe | Ser | Asp | Asp | Ser | Ile | Pro | Glu | Val | Pro | Gln | Thr |      |
|     |     |     |     |     | 725 |     |     |     |     | 730 |     |     |     |     | 735 |      |
| caa | gag | gag | gct | gtg | atg | ctc | atg | aag | gag | agt | ctc | act | gaa | gtg | tct | 2256 |
| Gln | Glu | Glu | Ala | Val | Met | Leu | Met | Lys | Glu | Ser | Leu | Thr | Glu | Val | Ser |      |
|     |     |     |     | 740 |     |     |     |     | 745 |     |     |     |     | 750 |     |      |
| gag | aca | gta | gcc | cag | cac | aaa | gag | gag | aga | ctt | agt | gcc | tca | cct | cag | 2304 |
| Glu | Thr | Val | Ala | Gln | His | Lys | Glu | Glu | Arg | Leu | Ser | Ala | Ser | Pro | Gln |      |
|     |     |     | 755 |     |     |     |     | 760 |     |     |     |     | 765 |     |     |      |
| gag | cta | gga | aag | cca | tat | tta | gag | tct | ttt | cag | ccc | aat | tta | cat | agt | 2352 |
| Glu | Leu | Gly | Lys | Pro | Tyr | Leu | Glu | Ser | Phe | Gln | Pro | Asn | Leu | His | Ser |      |
|     | 770 |     |     |     |     | 775 |     |     |     |     | 780 |     |     |     |     |      |
| aca | aaa | gat | gct | gca | tct | aat | gac | att | cca | aca | ttg | acc | aaa | aag | gag | 2400 |
| Thr | Lys | Asp | Ala | Ala | Ser | Asn | Asp | Ile | Pro | Thr | Leu | Thr | Lys | Lys | Glu |      |
| 785 |     |     |     |     | 790 |     |     |     |     | 795 |     |     |     |     | 800 |      |
| aaa | att | tct | ttg | caa | atg | gaa | gag | ttt | aat | act | gca | att | tat | tca | aat | 2448 |
| Lys | Ile | Ser | Leu | Gln | Met | Glu | Glu | Phe | Asn | Thr | Ala | Ile | Tyr | Ser | Asn |      |
|     |     |     |     | 805 |     |     |     |     | 810 |     |     |     |     | 815 |     |      |
| gat | gac | tta | ctt | tct | tct | aag | gaa | gac | aaa | ata | aaa | gaa | agt | gaa | aca | 2496 |
| Asp | Asp | Leu | Leu | Ser | Ser | Lys | Glu | Asp | Lys | Ile | Lys | Glu | Ser | Glu | Thr |      |
|     |     |     | 820 |     |     |     |     | 825 |     |     |     |     | 830 |     |     |      |
| ttt | tca | gat | tca | tct | ccg | att | gag | ata | ata | gat | gaa | ttt | ccc | acg | ttt | 2544 |
| Phe | Ser | Asp | Ser | Ser | Pro | Ile | Glu | Ile | Ile | Asp | Glu | Phe | Pro | Thr | Phe |      |
|     |     | 835 |     |     |     |     | 840 |     |     |     |     | 845 |     |     |     |      |
| gtc | agt | gct | aaa | gat | gat | tct | cct | aaa | tta | gcc | aag | gag | tac | act | gat | 2592 |
| Val | Ser | Ala | Lys | Asp | Asp | Ser | Pro | Lys | Leu | Ala | Lys | Glu | Tyr | Thr | Asp |      |
| 850 |     |     |     |     | 855 |     |     |     |     | 860 |     |     |     |     |     |      |
| cta | gaa | gta | tcc | gac | aaa | agt | gaa | att | gct | aat | atc | caa | agc | ggg | gca | 2640 |
| Leu | Glu | Val | Ser | Asp | Lys | Ser | Glu | Ile | Ala | Asn | Ile | Gln | Ser | Gly | Ala |      |
| 865 |     |     |     | 870 |     |     |     |     | 875 |     |     |     |     | 880 |     |      |
| gat | tca | ttg | cct | tgc | tta | gaa | ttg | ccc | tgt | gac | ctt | tct | ttc | aag | aat | 2688 |
| Asp | Ser | Leu | Pro | Cys | Leu | Glu | Leu | Pro | Cys | Asp | Leu | Ser | Phe | Lys | Asn |      |
|     |     |     | 885 |     |     |     |     | 890 |     |     |     |     | 895 |     |     |      |
| ata | tat | cct | aaa | gat | gaa | gta | cat | gtt | tca | gat | gaa | ttc | tcc | gaa | aat | 2736 |
| Ile | Tyr | Pro | Lys | Asp | Glu | Val | His | Val | Ser | Asp | Glu | Phe | Ser | Glu | Asn |      |
|     |     | 900 |     |     |     |     | 905 |     |     |     |     | 910 |     |     |     |      |
| agg | tcc | agt | gta | tct | aag | gca | tcc | ata | tcg | cct | tca | aat | gtc | tct | gct | 2784 |
| Arg | Ser | Ser | Val | Ser | Lys | Ala | Ser | Ile | Ser | Pro | Ser | Asn | Val | Ser | Ala |      |

```
                915                 920                 925
ttg gaa cct cag aca gaa atg ggc agc ata gtt aaa tcc aaa tca ctt      2832
Leu Glu Pro Gln Thr Glu Met Gly Ser Ile Val Lys Ser Lys Ser Leu
    930                 935                 940 acg aaa gaa gca gag aaa aaa ctt cct tct gac aca gag aaa gag gac      2880
Thr Lys Glu Ala Glu Lys Lys Leu Pro Ser Asp Thr Glu Lys Glu Asp
945                 950                 955                 960 aga tcc ctg tca gct gta ttg tca gca gag ctg agt aaa act tca gtt      2928
Arg Ser Leu Ser Ala Val Leu Ser Ala Glu Leu Ser Lys Thr Ser Val
                965                 970                 975 gtt gac ctc ctc tac tgg aga gac att aag aag act gga gtg gtg ttt      2976
Val Asp Leu Leu Tyr Trp Arg Asp Ile Lys Lys Thr Gly Val Val Phe
            980                 985                 990 ggt gcc agc tta ttc ctg ctg ctg  tct ctg aca gtg ttc  agc att gtc    3024
Gly Ala Ser Leu Phe Leu Leu Leu  Ser Leu Thr Val Phe  Ser Ile Val
                995                 1000                1005 agt gta  acg gcc tac att gcc  ttg gcc ctg ctc tcg  gtg act atc       3069
Ser Val  Thr Ala Tyr Ile Ala  Leu Ala Leu Leu Ser  Val Thr Ile
    1010                1015                1020 agc ttt  agg ata tat aag ggc  gtg atc cag gct atc  cag aaa tca       3114
Ser Phe  Arg Ile Tyr Lys Gly  Val Ile Gln Ala Ile  Gln Lys Ser
    1025                1030                1035 gat gaa  ggc cac cca ttc agg  gca tat tta gaa tct  gaa gtt gct       3159
Asp Glu  Gly His Pro Phe Arg  Ala Tyr Leu Glu Ser  Glu Val Ala
    1040                1045                1050 ata tca  gag gaa ttg gtt cag  aaa tac agt aat tct  gct ctt ggt       3204
Ile Ser  Glu Glu Leu Val Gln  Lys Tyr Ser Asn Ser  Ala Leu Gly
    1055                1060                1065 cat gtg  aac agc aca ata aaa  gaa ctg agg cgg ctt  ttc tta gtt       3249
His Val  Asn Ser Thr Ile Lys  Glu Leu Arg Arg Leu  Phe Leu Val
    1070                1075                1080 gat gat  tta gtt gat tcc ctg  aag ttt gca gtg ttg  atg tgg gtg       3294
Asp Asp  Leu Val Asp Ser Leu  Lys Phe Ala Val Leu  Met Trp Val
    1085                1090                1095 ttt act  tat gtt ggt gcc ttg  ttc aat ggt ctg aca  cta ctg att       3339
Phe Thr  Tyr Val Gly Ala Leu  Phe Asn Gly Leu Thr  Leu Leu Ile
    1100                1105                1110 tta gct  ctg atc tca ctc ttc  agt att cct gtt att  tat gaa cgg       3384
Leu Ala  Leu Ile Ser Leu Phe  Ser Ile Pro Val Ile  Tyr Glu Arg
    1115                1120                1125 cat cag  gtg cag ata gat cat  tat cta gga ctt gca  aac aag agt       3429
His Gln  Val Gln Ile Asp His  Tyr Leu Gly Leu Ala  Asn Lys Ser
    1130                1135                1140 gtt aag  gat gcc atg gcc aaa  atc caa gca aaa atc  cct gga ttg       3474
Val Lys  Asp Ala Met Ala Lys  Ile Gln Ala Lys Ile  Pro Gly Leu
    1145                1150                1155 aag cgc  aaa gca gat tga                                              3492
Lys Arg  Lys Ala Asp
    1160

<210> SEQ ID NO 26
<211> LENGTH: 1163
<212> TYPE: PRT
<213> ORGANISM: Rattus norvegicus

<400> SEQUENCE: 26

Met Glu Asp Ile Asp Gln Ser Ser Leu Val Ser Ser Ser Thr Asp Ser
1               5                   10                  15

Pro Pro Arg Pro Pro Ala Phe Lys Tyr Gln Phe Val Thr Glu Pro
            20                  25                  30
```

```
Glu Asp Glu Glu Asp Glu Glu Glu Asp Glu Glu Asp Asp
        35                  40                  45
Glu Asp Leu Glu Glu Leu Glu Val Leu Glu Arg Lys Pro Ala Ala Gly
    50                  55                  60
Leu Ser Ala Ala Ala Val Pro Pro Ala Ala Ala Pro Leu Leu Asp
65                  70                  75                  80
Phe Ser Ser Asp Ser Val Pro Pro Ala Pro Arg Gly Pro Leu Pro Ala
                85                  90                  95
Ala Pro Pro Ala Ala Pro Glu Arg Gln Pro Ser Trp Glu Arg Ser Pro
            100                 105                 110
Ala Ala Pro Ala Pro Ser Leu Pro Pro Ala Ala Val Leu Pro Ser
        115                 120                 125
Lys Leu Pro Glu Asp Asp Glu Pro Pro Ala Arg Pro Pro Pro Pro
    130                 135                 140
Pro Ala Gly Ala Ser Pro Leu Ala Glu Pro Ala Ala Pro Pro Ser Thr
145                 150                 155                 160
Pro Ala Ala Pro Lys Arg Arg Gly Ser Gly Ser Val Asp Glu Thr Leu
            165                 170                 175
Phe Ala Leu Pro Ala Ala Ser Glu Pro Val Ile Pro Ser Ser Ala Glu
            180                 185                 190
Lys Ile Met Asp Leu Met Glu Gln Pro Gly Asn Thr Val Ser Ser Gly
    195                 200                 205
Gln Glu Asp Phe Pro Ser Val Leu Leu Glu Thr Ala Ala Ser Leu Pro
    210                 215                 220
Ser Leu Ser Pro Leu Ser Thr Val Ser Phe Lys Glu His Gly Tyr Leu
225                 230                 235                 240
Gly Asn Leu Ser Ala Val Ser Ser Ser Glu Gly Thr Ile Glu Glu Thr
                245                 250                 255
Leu Asn Glu Ala Ser Lys Glu Leu Pro Glu Arg Ala Thr Asn Pro Phe
            260                 265                 270
Val Asn Arg Asp Leu Ala Glu Phe Ser Glu Leu Glu Tyr Ser Glu Met
        275                 280                 285
Gly Ser Ser Phe Lys Gly Ser Pro Lys Gly Glu Ser Ala Ile Leu Val
    290                 295                 300
Glu Asn Thr Lys Glu Glu Val Ile Val Arg Ser Lys Asp Lys Glu Asp
305                 310                 315                 320
Leu Val Cys Ser Ala Ala Leu His Ser Pro Gln Glu Ser Pro Val Gly
                325                 330                 335
Lys Glu Asp Arg Val Val Ser Pro Glu Lys Thr Met Asp Ile Phe Asn
            340                 345                 350
Glu Met Gln Met Ser Val Val Ala Pro Val Arg Glu Glu Tyr Ala Asp
        355                 360                 365
Phe Lys Pro Phe Glu Gln Ala Trp Glu Val Lys Asp Thr Tyr Glu Gly
    370                 375                 380
Ser Arg Asp Val Leu Ala Ala Arg Ala Asn Val Glu Ser Lys Val Asp
385                 390                 395                 400
Arg Lys Cys Leu Glu Asp Ser Leu Glu Gln Lys Ser Leu Gly Lys Asp
                405                 410                 415
Ser Glu Gly Arg Asn Glu Asp Ala Ser Phe Pro Ser Thr Pro Glu Pro
            420                 425                 430
Val Lys Asp Ser Ser Arg Ala Tyr Ile Thr Cys Ala Ser Phe Thr Ser
        435                 440                 445
```

-continued

```
Ala Thr Glu Ser Thr Thr Ala Asn Thr Phe Pro Leu Leu Glu Asp His
    450                 455                 460

Thr Ser Glu Asn Lys Thr Asp Glu Lys Lys Ile Glu Glu Arg Lys Ala
465                 470                 475                 480

Gln Ile Ile Thr Glu Lys Thr Ser Pro Lys Thr Ser Asn Pro Phe Leu
                    485                 490                 495

Val Ala Val Gln Asp Ser Glu Ala Asp Tyr Val Thr Thr Asp Thr Leu
                500                 505                 510

Ser Lys Val Thr Glu Ala Ala Val Ser Asn Met Pro Glu Gly Leu Thr
            515                 520                 525

Pro Asp Leu Val Gln Glu Ala Cys Glu Ser Glu Leu Asn Glu Ala Thr
        530                 535                 540

Gly Thr Lys Ile Ala Tyr Glu Thr Lys Val Asp Leu Val Gln Thr Ser
545                 550                 555                 560

Glu Ala Ile Gln Glu Ser Leu Tyr Pro Thr Ala Gln Leu Cys Pro Ser
                    565                 570                 575

Phe Glu Glu Ala Glu Ala Thr Pro Ser Pro Val Leu Pro Asp Ile Val
                580                 585                 590

Met Glu Ala Pro Leu Asn Ser Leu Leu Pro Ser Ala Gly Ala Ser Val
            595                 600                 605

Val Gln Pro Ser Val Ser Pro Leu Glu Ala Pro Pro Pro Val Ser Tyr
        610                 615                 620

Asp Ser Ile Lys Leu Glu Pro Glu Asn Pro Pro Pro Tyr Glu Glu Ala
625                 630                 635                 640

Met Asn Val Ala Leu Lys Ala Leu Gly Thr Lys Glu Gly Ile Lys Glu
                    645                 650                 655

Pro Glu Ser Phe Asn Ala Ala Val Gln Glu Thr Glu Ala Pro Tyr Ile
                660                 665                 670

Ser Ile Ala Cys Asp Leu Ile Lys Glu Thr Lys Leu Ser Thr Glu Pro
            675                 680                 685

Ser Pro Asp Phe Ser Asn Tyr Ser Glu Ile Ala Lys Phe Glu Lys Ser
        690                 695                 700

Val Pro Glu His Ala Glu Leu Val Glu Asp Ser Ser Pro Glu Ser Glu
705                 710                 715                 720

Pro Val Asp Leu Phe Ser Asp Asp Ser Ile Pro Glu Val Pro Gln Thr
                    725                 730                 735

Gln Glu Glu Ala Val Met Leu Met Lys Glu Ser Leu Thr Glu Val Ser
                740                 745                 750

Glu Thr Val Ala Gln His Lys Glu Glu Arg Leu Ser Ala Ser Pro Gln
            755                 760                 765

Glu Leu Gly Lys Pro Tyr Leu Glu Ser Phe Gln Pro Asn Leu His Ser
        770                 775                 780

Thr Lys Asp Ala Ala Ser Asn Asp Ile Pro Thr Leu Thr Lys Lys Glu
785                 790                 795                 800

Lys Ile Ser Leu Gln Met Glu Glu Phe Asn Thr Ala Ile Tyr Ser Asn
                    805                 810                 815

Asp Asp Leu Leu Ser Ser Lys Glu Asp Lys Ile Lys Glu Ser Glu Thr
                820                 825                 830

Phe Ser Asp Ser Ser Pro Ile Glu Ile Asp Glu Phe Pro Thr Phe
            835                 840                 845

Val Ser Ala Lys Asp Asp Ser Pro Lys Leu Ala Lys Glu Tyr Thr Asp
        850                 855                 860

Leu Glu Val Ser Asp Lys Ser Glu Ile Ala Asn Ile Gln Ser Gly Ala
```

```
                865                 870                 875                 880
Asp Ser Leu Pro Cys Leu Glu Leu Pro Cys Asp Leu Ser Phe Lys Asn
                    885                 890                 895
Ile Tyr Pro Lys Asp Glu Val His Val Ser Asp Glu Phe Ser Glu Asn
                900                 905                 910
Arg Ser Val Ser Lys Ala Ser Ile Ser Pro Ser Asn Val Ser Ala
            915                 920                 925
Leu Glu Pro Gln Thr Glu Met Gly Ser Ile Val Lys Ser Lys Ser Leu
        930                 935                 940
Thr Lys Glu Ala Glu Lys Lys Leu Pro Ser Asp Thr Glu Lys Glu Asp
945                 950                 955                 960
Arg Ser Leu Ser Ala Val Leu Ser Ala Glu Leu Ser Lys Thr Ser Val
                965                 970                 975
Val Asp Leu Leu Tyr Trp Arg Asp Ile Lys Lys Thr Gly Val Val Phe
            980                 985                 990
Gly Ala Ser Leu Phe Leu Leu Leu Ser Leu Thr Val Phe Ser Ile Val
        995                 1000                1005
Ser Val Thr Ala Tyr Ile Ala Leu Ala Leu Leu Ser Val Thr Ile
    1010                1015                1020
Ser Phe Arg Ile Tyr Lys Gly Val Ile Gln Ala Ile Gln Lys Ser
    1025                1030                1035
Asp Glu Gly His Pro Phe Arg Ala Tyr Leu Glu Ser Glu Val Ala
    1040                1045                1050
Ile Ser Glu Glu Leu Val Gln Lys Tyr Ser Asn Ser Ala Leu Gly
    1055                1060                1065
His Val Asn Ser Thr Ile Lys Glu Leu Arg Arg Leu Phe Leu Val
    1070                1075                1080
Asp Asp Leu Val Asp Ser Leu Lys Phe Ala Val Leu Met Trp Val
    1085                1090                1095
Phe Thr Tyr Val Gly Ala Leu Phe Asn Gly Leu Thr Leu Leu Ile
    1100                1105                1110
Leu Ala Leu Ile Ser Leu Phe Ser Ile Pro Val Ile Tyr Glu Arg
    1115                1120                1125
His Gln Val Gln Ile Asp His Tyr Leu Gly Leu Ala Asn Lys Ser
    1130                1135                1140
Val Lys Asp Ala Met Ala Lys Ile Gln Ala Lys Ile Pro Gly Leu
    1145                1150                1155
Lys Arg Lys Ala Asp
    1160

<210> SEQ ID NO 27
<211> LENGTH: 25
<212> TYPE: PRT
<213> ORGANISM: Rattus norvegicus
<220> FEATURE:
<221> NAME/KEY: PEPTIDE
<222> LOCATION: (1)..(25)
<223> OTHER INFORMATION: rat PEP4

<400> SEQUENCE: 27

Glu Glu Leu Val Gln Lys Tyr Ser Asn Ser Ala Leu Gly His Val Asn
1               5                   10                  15

Ser Thr Ile Lys Glu Leu Arg Arg Leu
            20                  25

<210> SEQ ID NO 28
```

-continued

```
<211> LENGTH: 17
<212> TYPE: PRT
<213> ORGANISM: Artificial Sequence
<220> FEATURE:
<223> OTHER INFORMATION: PRO/SER rich peptide
<220> FEATURE:
<221> NAME/KEY: PEPTIDE
<222> LOCATION: (1)..(17)
<223> OTHER INFORMATION: Synthetic peptide

<400> SEQUENCE: 28

Pro Ser Ser Pro Pro Pro Ser Ser Pro Pro Pro Ser Ser Pro Pro Pro
1               5                   10                  15

Ser

<210> SEQ ID NO 29
<211> LENGTH: 25
<212> TYPE: DNA
<213> ORGANISM: Artificial Sequence
<220> FEATURE:
<223> OTHER INFORMATION: CA-NA-2F
<220> FEATURE:
<221> NAME/KEY: primer_bind
<222> LOCATION: (1)..(25)
<223> OTHER INFORMATION: CA-NA-2F primer

<400> SEQUENCE: 29
aagcaccatt gaattctgca gttcc                                         25

<210> SEQ ID NO 30
<211> LENGTH: 28
<212> TYPE: DNA
<213> ORGANISM: Artificial Sequence
<220> FEATURE:
<223> OTHER INFORMATION: CA-NA-3R
<220> FEATURE:
<221> NAME/KEY: primer_bind
<222> LOCATION: (1)..(28)

<400> SEQUENCE: 30
aactgcagta ctgagctcct ccatctgc                                      28

<210> SEQ ID NO 31
<211> LENGTH: 33
<212> TYPE: DNA
<213> ORGANISM: Artificial Sequence
<220> FEATURE:
<223> OTHER INFORMATION: forward 5'
<220> FEATURE:
<221> NAME/KEY: primer_bind
<222> LOCATION: (1)..(33)
<223> OTHER INFORMATION: forward primer

<400> SEQUENCE: 31
gtcgcggatc catggagacc cttttttgctc ttc                                33

<210> SEQ ID NO 32
<211> LENGTH: 27
<212> TYPE: DNA
<213> ORGANISM: Artificial Sequence
<220> FEATURE:
<223> OTHER INFORMATION: reverse 5'
<220> FEATURE:
<221> NAME/KEY: primer_bind
<222> LOCATION: (1)..(27)
<223> OTHER INFORMATION: reverse primer

<400> SEQUENCE: 32
gttctcgagt tatgaagttt tactcag                                       27
```

<210> SEQ ID NO 33
<211> LENGTH: 29
<212> TYPE: DNA
<213> ORGANISM: Artificial Sequence
<220> FEATURE:
<223> OTHER INFORMATION: forward 5'-1
<220> FEATURE:
<221> NAME/KEY: primer_bind
<222> LOCATION: (1)..(29)
<223> OTHER INFORMATION: primer

<400> SEQUENCE: 33
gtgcggatcc atggatttga aggagcagc                                    29

<210> SEQ ID NO 34
<211> LENGTH: 28
<212> TYPE: DNA
<213> ORGANISM: Artificial Sequence
<220> FEATURE:
<223> OTHER INFORMATION: reverse 5'-1
<220> FEATURE:
<221> NAME/KEY: primer_bind
<222> LOCATION: (1)..(28)
<223> OTHER INFORMATION: primer

<400> SEQUENCE: 34
gtttctcgag tgaagtttta ttcagctc                                     28

<210> SEQ ID NO 35
<211> LENGTH: 20
<212> TYPE: DNA
<213> ORGANISM: Artificial Sequence
<220> FEATURE:
<223> OTHER INFORMATION: 5' primer
<220> FEATURE:
<221> NAME/KEY: primer_bind
<222> LOCATION: (1)..(20)
<223> OTHER INFORMATION: primer

<400> SEQUENCE: 35
tccaccccgg ccgcgcccaa                                              20

<210> SEQ ID NO 36
<211> LENGTH: 22
<212> TYPE: DNA
<213> ORGANISM: Artificial Sequence
<220> FEATURE:
<223> OTHER INFORMATION: 5' primer 2
<220> FEATURE:
<221> NAME/KEY: primer_bind
<222> LOCATION: (1)..(22)
<223> OTHER INFORMATION: primer

<400> SEQUENCE: 36
aatgatgggc aaagctgtgc tg                                           22

<210> SEQ ID NO 37
<211> LENGTH: 24
<212> TYPE: DNA
<213> ORGANISM: Artificial Sequence
<220> FEATURE:
<223> OTHER INFORMATION: 3' primer
<220> FEATURE:
<221> NAME/KEY: primer_bind
<222> LOCATION: (1)..(24)
<223> OTHER INFORMATION: primer

<400> SEQUENCE: 37
ggtacaaaga ttgcttatga aaca                                            24

<210> SEQ ID NO 38
<211> LENGTH: 22
<212> TYPE: DNA
<213> ORGANISM: Artificial Sequence
<220> FEATURE:
<223> OTHER INFORMATION: 3' primer 2
<220> FEATURE:
<221> NAME/KEY: primer_bind
<222> LOCATION: (1)..(22)
<223> OTHER INFORMATION: primer

<400> SEQUENCE: 38
agcagggcca aggcaatgta gg                                              22

<210> SEQ ID NO 39
<211> LENGTH: 28
<212> TYPE: DNA
<213> ORGANISM: Artificial Sequence
<220> FEATURE:
<223> OTHER INFORMATION: 5'-VL leader
<220> FEATURE:
<221> NAME/KEY: primer_bind
<222> LOCATION: (1)..(28)
<223> OTHER INFORMATION: primer

<400> SEQUENCE: 39
aatatgagtc ctgcccagtt cctgtttc                                        28

<210> SEQ ID NO 40
<211> LENGTH: 32
<212> TYPE: DNA
<213> ORGANISM: Artificial Sequence
<220> FEATURE:
<223> OTHER INFORMATION: 3'-Ck
<220> FEATURE:
<221> NAME/KEY: primer_bind
<222> LOCATION: (1)..(32)
<223> OTHER INFORMATION: primer

<400> SEQUENCE: 40
ttaggaattc ctaacactct cccctgttga ag                                   32

<210> SEQ ID NO 41
<211> LENGTH: 31
<212> TYPE: DNA
<213> ORGANISM: Artificial Sequence
<220> FEATURE:
<223> OTHER INFORMATION: 5'-VH leader
<220> FEATURE:
<221> NAME/KEY: primer_bind
<222> LOCATION: (1)..(31)
<223> OTHER INFORMATION: primer

<400> SEQUENCE: 41
aatatggatt tgggctgat ttttttatt g                                      31

<210> SEQ ID NO 42
<211> LENGTH: 24
<212> TYPE: DNA
<213> ORGANISM: Artificial Sequence
<220> FEATURE:
<223> OTHER INFORMATION: 3'-CH hinge
<220> FEATURE:
<221> NAME/KEY: primer_bind
<222> LOCATION: (1)..(24)
<223> OTHER INFORMATION: primer

<400> SEQUENCE: 42

```
aattgggcaa cgttgcaggt gacg                                         24

<210> SEQ ID NO 43
<211> LENGTH: 663
<212> TYPE: DNA
<213> ORGANISM: Mus musculus
<220> FEATURE:
<221> NAME/KEY: misc_binding
<222> LOCATION: (1)..(663)
<223> OTHER INFORMATION: DNA variable part of heavy chain 11C7

<400> SEQUENCE: 43
atggattttg ggctgatttt ttttattgtt ggtcttttaa aaggggtcca gtgtgaggtg    60
aagcttctcg agtctggagg tggcctggtg cagcctggag gatccctgaa actctcctgt   120
gtagtctcag gattcgattt tagaagaaat tggatgagtt gggtccggca ggctcctggg   180
aaagggctag aatggattgg agaaattaat ccagatagca gtaagataaa ctatacgcca   240
tctctaaagg ataaattcat catctccaga gacaatgcca gaatacgct gtacctgcaa    300 gtgagcacag tgagatctga ggacacagcc ctttattact gtgtgagacc ggtctggatg   360
tatgctatgg actactgggg tcaaggaacc tcagtcaccg tctcctcagc caaaacgaca   420
cccccatctg tctatccact ggcccctgga tctgctgccc aaactaactc catggtgacc   480
ctgggatgcc tggtcaaggg ctatttccct gagccagtga cagtgacctg gaactctgga   540
tccctgtcca gcggtgtgca caccttccca gctgtcctgc agtctgacct ctacactctg   600
agcagctcag tgactgtccc ctccagcacc tggcccagcg agaccgtcac ctgcaacgtt   660
gcc                                                                663

<210> SEQ ID NO 44
<211> LENGTH: 717
<212> TYPE: DNA
<213> ORGANISM: Mus musculus
<220> FEATURE:
<221> NAME/KEY: misc_binding
<222> LOCATION: (1)..(717)
<223> OTHER INFORMATION: variable part of light chain of 11C7

<400> SEQUENCE: 44
atgagtcctg cccagttcct gtttctgtta gtgctctgga ttcgggaaac cagcggtgat    60
gttctgttga cccagactcc tctcactttg tcgataacca ttggacaacc agcctccatc   120
tcttgcaagt caagtcagag cctcttgcat agtgatggaa agacatattt gaattggttg   180
ttacagaggc caggccagtc tccaaagcgc ctaatctatc tggtgtctaa actggactct   240
ggagtccctg acaggttcac tggcagtgga tcagggacgg atttcacact gaaaatcagc   300
agagtggagg ctgaggattt ggactttat tattgctggc aaggtacaca ttttcctcag    360
acgttcggtg gaggcaccaa gctggaaatc aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc     660 actcacaaga catcaacttc acccattgtc aagagcttca cagggaga gtgttag        717

<210> SEQ ID NO 45
<211> LENGTH: 239
<212> TYPE: PRT
```

<213> ORGANISM: Homo sapiens

<400> SEQUENCE: 45

```
Thr Lys Val Thr Glu Val Val Ala Asn Met Pro Glu Gly Leu Thr
1               5                   10                  15

Pro Asp Leu Val Gln Glu Ala Cys Glu Ser Glu Leu Asn Glu Val Thr
                20                  25                  30

Gly Thr Lys Ile Ala Tyr Glu Thr Lys Met Asp Leu Val Gln Thr Ser
            35                  40                  45

Glu Val Met Gln Glu Ser Leu Tyr Pro Ala Ala Gln Leu Cys Pro Ser
        50                  55                  60

Phe Glu Glu Ser Glu Ala Thr Pro Ser Pro Val Leu Pro Asp Ile Val
65                  70                  75                  80

Met Glu Ala Pro Leu Asn Ser Ala Val Pro Ser Ala Gly Ala Ser Val
                85                  90                  95

Ile Gln Pro Ser Ser Ser Pro Leu Glu Ala Ser Ser Val Asn Tyr Glu
            100                 105                 110

Ser Ile Lys His Glu Pro Glu Asn Pro Pro Tyr Glu Glu Ala Met
        115                 120                 125

Ser Val Ser Leu Lys Lys Val Ser Gly Ile Lys Glu Glu Ile Lys Glu
    130                 135                 140

Pro Glu Asn Ile Asn Ala Ala Leu Gln Glu Thr Glu Ala Pro Tyr Ile
145                 150                 155                 160

Ser Ile Ala Cys Asp Leu Ile Lys Glu Thr Lys Leu Ser Ala Glu Pro
                165                 170                 175

Ala Pro Asp Phe Ser Asp Tyr Ser Glu Met Ala Lys Val Glu Gln Pro
            180                 185                 190

Val Pro Asp His Ser Glu Leu Val Glu Asp Ser Ser Pro Asp Ser Glu
        195                 200                 205

Pro Val Asp Leu Phe Ser Asp Ser Ile Pro Asp Val Pro Gln Lys
    210                 215                 220

Gln Asp Glu Thr Val Met Leu Val Lys Glu Ser Leu Thr Glu Thr
225                 230                 235
```

<210> SEQ ID NO 46
<211> LENGTH: 239
<212> TYPE: PRT
<213> ORGANISM: Pan paniscus

<400> SEQUENCE: 46

```
Gly Lys Val Thr Glu Val Val Ala Asn Met Pro Glu Gly Leu Thr
1               5                   10                  15

Pro Asp Leu Val Gln Glu Ala Cys Glu Ser Glu Leu Asn Glu Val Thr
                20                  25                  30

Gly Thr Lys Ile Ala Tyr Glu Thr Lys Met Asp Leu Val Gln Thr Ser
            35                  40                  45

Glu Val Met Gln Glu Ser Leu Tyr Pro Ala Ala Gln Leu Cys Pro Ser
        50                  55                  60

Phe Glu Glu Ser Glu Ala Thr Pro Ser Pro Val Leu Pro Asp Ile Val
65                  70                  75                  80

Met Glu Ala Pro Leu Asn Ser Ala Val Pro Ser Ala Gly Ala Ser Ala
                85                  90                  95

Val Gln Pro Ser Ser Ser Pro Leu Glu Ala Ser Ser Val Asn Tyr Glu
            100                 105                 110

Ser Ile Ile His Glu Pro Glu Asn Pro Pro Tyr Glu Glu Ala Met
```

-continued

```
                115                 120                 125
Ser Val Ser Leu Lys Lys Val Ser Gly Ile Lys Glu Glu Ile Lys Glu
            130                 135                 140

Pro Glu Ser Ile Asn Ala Ala Val Gln Glu Thr Glu Ala Pro Tyr Ile
145                 150                 155                 160

Ser Ile Ala Cys Asp Leu Ile Lys Glu Thr Lys Leu Ser Ala Glu Pro
                165                 170                 175

Thr Pro Asp Phe Ser Asp Tyr Ser Glu Met Ala Lys Val Glu Gln Pro
            180                 185                 190

Val Pro Asp His Ser Glu Leu Val Glu Asp Ser Ser Pro Asp Ser Glu
            195                 200                 205

Pro Val Asp Leu Phe Ser Asp Ser Ile Pro Asp Val Pro Gln Lys
210                 215                 220

Gln Asp Glu Ala Val Met Leu Val Lys Glu Asn Leu Pro Glu Thr
225                 230                 235

<210> SEQ ID NO 47
<211> LENGTH: 239
<212> TYPE: PRT
<213> ORGANISM: Rattus norvegicus

<400> SEQUENCE: 47

Ser Lys Val Thr Glu Ala Ala Val Ser Asn Met Pro Glu Gly Leu Thr
1               5                   10                  15

Pro Asp Leu Val Gln Glu Ala Cys Glu Ser Glu Leu Asn Glu Ala Thr
            20                  25                  30

Gly Thr Lys Ile Ala Tyr Glu Thr Lys Val Asp Leu Val Gln Thr Ser
        35                  40                  45

Glu Ala Ile Gln Glu Ser Leu Tyr Pro Thr Ala Gln Leu Cys Pro Ser
    50                  55                  60

Phe Glu Glu Ala Glu Ala Thr Pro Ser Pro Val Leu Pro Asp Ile Val
65                  70                  75                  80

Met Glu Ala Pro Leu Asn Ser Leu Leu Pro Ser Ala Gly Ala Ser Val
                85                  90                  95

Val Gln Pro Ser Val Ser Pro Leu Glu Ala Pro Pro Val Ser Tyr
            100                 105                 110

Asp Ser Ile Lys Leu Glu Pro Glu Asn Pro Pro Tyr Glu Glu Ala
        115                 120                 125

Met Asn Val Ala Leu Lys Ala Leu Gly Thr Lys Glu Gly Ile Lys Glu
    130                 135                 140

Pro Glu Ser Phe Asn Ala Ala Val Gln Glu Thr Glu Ala Pro Tyr Ile
145                 150                 155                 160

Ser Ile Ala Cys Asp Leu Ile Lys Glu Thr Lys Leu Ser Thr Glu Pro
                165                 170                 175

Ser Pro Asp Phe Ser Asn Tyr Ser Glu Ile Ala Lys Phe Glu Lys Ser
            180                 185                 190

Val Pro Glu His Ala Glu Leu Val Glu Asp Ser Ser Pro Glu Ser Glu
            195                 200                 205

Pro Val Asp Leu Phe Ser Asp Asp Ser Ile Pro Glu Val Pro Gln Thr
210                 215                 220

Gln Glu Glu Ala Val Met Leu Met Lys Glu Ser Leu Thr Glu Val
225                 230                 235

<210> SEQ ID NO 48
<211> LENGTH: 239
```

```
<212> TYPE: PRT
<213> ORGANISM: Mus musculus

<400> SEQUENCE: 48

Ser Lys Val Thr Glu Ala Val Val Ala Thr Met Pro Glu Gly Leu Thr
1               5                   10                  15

Pro Asp Leu Val Gln Glu Ala Cys Glu Ser Glu Leu Asn Glu Ala Thr
            20                  25                  30

Gly Thr Lys Ile Ala Tyr Glu Thr Lys Val Asp Leu Val Gln Thr Ser
        35                  40                  45

Glu Ala Ile Gln Glu Ser Ile Tyr Pro Thr Ala Gln Leu Cys Pro Ser
    50                  55                  60

Phe Glu Glu Ala Glu Ala Thr Pro Ser Pro Val Leu Pro Asp Ile Val
65                  70                  75                  80

Met Glu Ala Pro Leu Asn Ser Leu Leu Pro Ser Thr Gly Ala Ser Val
                85                  90                  95

Ala Gln Pro Ser Ala Ser Pro Leu Glu Val Pro Ser Pro Val Ser Tyr
            100                 105                 110

Asp Gly Ile Lys Leu Glu Pro Glu Asn Pro Pro Tyr Glu Glu Ala
        115                 120                 125

Met Ser Val Ala Leu Lys Thr Ser Asp Ser Lys Glu Glu Ile Lys Glu
    130                 135                 140

Pro Glu Ser Phe Asn Ala Ala Gln Glu Ala Glu Ala Pro Tyr Ile
145                 150                 155                 160

Ser Ile Ala Cys Asp Leu Ile Lys Glu Thr Lys Leu Ser Thr Glu Pro
                165                 170                 175

Ser Pro Glu Phe Ser Asn Tyr Ser Glu Ile Ala Lys Phe Glu Lys Ser
            180                 185                 190

Val Pro Asp His Cys Glu Leu Val Asp Asp Ser Ser Pro Glu Ser Glu
        195                 200                 205

Pro Val Asp Leu Phe Ser Asp Asp Ser Ile Pro Glu Val Pro Gln Thr
    210                 215                 220

Gln Glu Glu Ala Val Met Leu Met Lys Glu Ser Leu Thr Glu Val
225                 230                 235
```